US005968404A

United States Patent [19]
Trinh et al.

[11] Patent Number: 5,968,404
[45] Date of Patent: Oct. 19, 1999

[54] UNCOMPLEXED CYCLODEXTRIN COMPOSITIONS FOR ODOR AND WRINKLE CONTROL

[75] Inventors: Toan Trinh; Raymond Edward Bolich, Jr., both of Maineville; Helen Bernardo Tordil, West Chester; Robert Mermelstein; Marjorie Mossman Peffly, both of Cincinnati; Ricky Ah-Man Woo, Hamilton; Daniel Scott Cobb, Loveland; Eva Schneiderman, Fairfield; Ann Margaret Wolff, Cincinnati; Erin Lynn Rosenbalm, Fairfield; Thomas Edward Ward, Oxford; Alex Haejoon Chung, West Chester; Anthony James Burns, West Chester; William Tucker Campbell, West Chester, all of Ohio; Alen David Streutker, Florence, Ky.

[73] Assignee: The Procter & Gamble Company, Cincinnati, Ohio

[21] Appl. No.: 09/067,182

[22] Filed: Apr. 27, 1998

Related U.S. Application Data

[63] Continuation-in-part of application No. 08/871,576, Jun. 9, 1997.

[51] Int. Cl.⁶ .............................. D06M 15/03; C08L 5/16; C11D 3/22; C11D 17/00
[52] U.S. Cl. ...................... 252/8.91; 252/8.61; 424/76.1; 424/76.2; 510/101; 510/293; 510/319; 510/383; 510/386; 510/405; 510/406; 510/462; 510/470; 510/513; 106/205.01; 106/205.1; 422/5
[58] Field of Search ................................. 252/8.91, 8.61; 424/76.1, 76.2; 510/101, 293, 383, 386, 319, 405, 406, 462, 470, 513; 106/205.01, 205.1; 422/5

[56] References Cited

U.S. PATENT DOCUMENTS

| | | | |
|---|---|---|---|
| 2,544,093 | 3/1951 | Kilgore | 252/1 |
| 3,074,891 | 1/1963 | Kulka | 252/305 |
| 4,085,243 | 4/1978 | Giordano et al. | 427/387 |
| 4,278,658 | 7/1981 | Hooper et al. | 424/65 |
| 4,382,079 | 5/1983 | Marschner | 424/65 |
| 4,904,524 | 2/1990 | Yoh | 428/311.3 |
| 5,094,761 | 3/1992 | Trinh et al. | 252/8.9 |
| 5,173,201 | 12/1992 | Coffindaffer et al. | 252/8.8 |
| 5,184,778 | 2/1993 | Noakes | 239/691 |
| 5,199,953 | 4/1993 | Fung et al. | 8/120 |
| 5,429,628 | 7/1995 | Trinh et al. | 604/359 |
| 5,464,545 | 11/1995 | Isharani et al. | 252/8.6 |
| 5,486,355 | 1/1996 | Berschied, Jr. | 424/65 |
| 5,512,199 | 4/1996 | Khan et al. | 252/106 |
| 5,518,727 | 5/1996 | Lajoie et al. | 424/400 |
| 5,532,023 | 7/1996 | Vogel et al. | 427/8 |
| 5,534,165 | 7/1996 | Pilosof et al. | 252/8.91 |
| 5,540,853 | 7/1996 | Trinh et al. | 510/101 |
| 5,552,378 | 9/1996 | Trinh et al. | 512/3 |
| 5,578,563 | 11/1996 | Trinh et al. | 510/513 |
| 5,593,670 | 1/1997 | Trinh et al. | 424/76.1 |
| 5,614,591 | 3/1997 | Basinger et al. | 525/163 |
| 5,620,787 | 4/1997 | Ona et al. | 442/102 |
| 5,645,751 | 7/1997 | Haley | 252/8.91 |
| 5,663,134 | 9/1997 | Trinh et al. | 510/406 |
| 5,668,097 | 9/1997 | Trinh et al. | 510/293 |
| 5,670,475 | 9/1997 | Trinh et al. | 510/470 |
| 5,695,677 | 12/1997 | Silvester et al. | 252/8.91 |
| 5,714,137 | 2/1998 | Trinh et al. | 424/76.4 |
| 5,783,544 | 7/1998 | Trinh et al. | 510/293 |
| 5,798,107 | 8/1998 | Vogel et al. | 424/400 |

FOREIGN PATENT DOCUMENTS

| | | | |
|---|---|---|---|
| 0 367 039 A2 | 5/1990 | European Pat. Off. | D06M 15/693 |
| 0 378 871 A2 | 7/1990 | European Pat. Off. | D06M 15/643 |
| 0 354 648 B1 | 6/1994 | European Pat. Off. | D06M 13/192 |
| 0 613 675 A1 | 9/1994 | European Pat. Off. | A61K 31/44 |
| 2201880 | 5/1974 | France | A61K 27/00 |
| 2731520 | 1/1979 | Germany | A61K 7/32 |
| 53-41440 | 4/1978 | Japan | A61K 7/32 |
| 58-124452 | 7/1983 | Japan | A61L 9/01 |
| 61-128973 | 6/1986 | Japan . | |
| 63-164953 | 7/1988 | Japan . | |
| 3-170415 | 7/1991 | Japan . | |
| 3-284616 | 12/1991 | Japan | A61K 7/16 |
| 5-269185 | 10/1993 | Japan | A61L 9/01 |
| WO 96/04940 | 2/1996 | WIPO | A61L 9/01 |
| WO 95/17175 | 6/1996 | WIPO | A61K 9/70 |

OTHER PUBLICATIONS

Hashimoto, H., "Studies on the Industrial Production and Application of Cyclodextrins", Starch Science, vol. 36, No. 1 (1989), pp. 35–42. No Month.

Hashimoto, H., "Application of Cyclodextrins to Foods, Toiletries and Other Products in Japan", Ensuiko Sugar Refining Co., Ltd., pp. 13–46. No Date.

*Primary Examiner*—Anthony Green
*Attorney, Agent, or Firm*—Robert B. Aylor

[57] ABSTRACT

The present invention relates to a stable, aqueous odor-absorbing and wrinkle controlling composition, preferably for use on inanimate surfaces, especially fabrics. The composition comprises from about 0.1% to about 20%, by weight of the composition, of solubilized, water-soluble, uncomplexed cyclodextrin and an effective amount of at least one ingredient to improve the performance of the composition selected from the group consisting of: (1) cyclodextrin compatible surfactant; (2) cyclodextrin compatible antimicrobial active; and (3) mixtures thereof. The composition also comprises a wrinkle control agent which is fabric lubricant, shape retention polymer, hydrophilic plasticizer, lithium salt, or mixtures thereof. Hydrophilic perfume improves acceptance. Optionally, the composition can contain low molecular weight polyols; metallic salts to help control odor; a humectant, etc. The composition is essentially free of any material that would soil or stain fabric. The composition is preferably applied as small particle size droplets, especially from spray containers. The cyclodextrin/surfactant combination, either alone, or in combination with the other ingredients, provides improved antimicrobial activity.

49 Claims, No Drawings

UNCOMPLEXED CYCLODEXTRIN COMPOSITIONS FOR ODOR AND WRINKLE CONTROL

This application is a continuation-in-part of application Ser. No. 08/871,576, filed on Jun. 9, 1997.

TECHNICAL FIELD

The present invention relates to stable, preferably translucent, more preferably clear, aqueous odor-absorbing and wrinkle controlling compositions, articles of manufacture, and/or method of use, comprising solubilized, uncomplexed cyclodextrin; and cyclodextrin-compatible fabric wrinkle control agent; and, preferably, cyclodextrin compatible antimicrobial active and/or cyclodextrin compatible surfactant;, hydrophilic perfume providing improved acceptance; or mixtures thereof. As used herein, "cyclodextrin compatible" means that the cyclodextrin and the other material, or active, do not substantially interact so as to eliminate the odor controlling ability of the cyclodextrin or the desired effect of the material or active. The odor-absorbing composition is designed to control odors caused by a broad spectrum of organic odoriferous materials, which may, or may not, contain reactive functional groups, and to preferably remain shelf stable for a substantial period of time. Preferably, the aqueous odor-absorbing compositions are for use on inanimate surfaces, especially fabrics, and more specifically, clothes, in order to restore and/or maintain freshness by reducing malodor without the need for washing or dry cleaning.

BACKGROUND OF THE INVENTION

The present invention relates to stable, preferably translucent, more preferably clear, aqueous odor absorbing and wrinkle controlling compositions, articles of manufacture and/or method for use, e.g., on inanimate surfaces, primarily fabrics, and especially cotton fabrics. Such compositions can optionally provide a "scent signal" in the form of a pleasant odor which signals the removal of the malodor. Preferably, the compositions are sprayed onto fabrics, particularly clothes, to restore their freshness by reducing malodor and/or removing wrinkles without washing or dry cleaning. The aqueous odor-absorbing compositions are also preferably for use on other inanimate surfaces, such as household upholsteries, drapes, carpets, car interiors, and the like. They also can be used on, e.g., human and animal surfaces, e.g., skin, hair, etc.

Uncomplexed cyclodextrin molecules, which are made up of varying numbers of glucose units provide the absorbing advantages of known absorbent deodorizing compositions without harmful effects to fabrics. While cyclodextrin is an effective odor absorbing active, some small molecules are not sufficiently absorbed by the cyclodextrin molecules because the cavity of the cyclodextrin molecule may be too large to adequately hold the smaller organic molecule. If a small sized organic odor molecule is not sufficiently absorbed into the cyclodextrin cavity, a substantial amount of malodor can remain. In order to alleviate this problem, low molecular weight polyols can be added to the composition to enhance the formation of cyclodextrin inclusion complexes. Furthermore, optional water soluble metal salts can be added to complex with some nitrogen-containing and sulfur-containing malodor molecules.

Since cyclodextrin is a prime breeding ground for certain microorganisms, especially when in aqueous compositions, it is preferable to include a water-soluble antimicrobial preservative, which is effective for inhibiting and/or regulating microbial growth, to increase storage stability of clear, aqueous odor-absorbing solutions containing water-soluble cyclodextrin, when the composition does not contain an antimicrobial material as described hereinafter.

It is desirable to provide further improvements such as a cyclodextrin compatible antimicrobial active that provides substantial kill of organisms that cause, e.g., odor, infections, etc. It is also desirable that the compositions contain a cyclodextrin compatible surfactant to promote spreading of the odor absorbing composition on hydrophobic surfaces such as polyester, nylon, etc. as well as to penetrate any oily, hydrophobic soil for improved malodor control. Furthermore, it is desirable that the cyclodextrin-compatible surfactant provide in-wear electrostatic control. It is more preferable that the odor absorbing composition of the present invention contain both a cyclodextrin-compatible antibacterial active and a cyclodextrin-compatible surfactant. A cyclodextrin-compatible active is one which does not substantially form a complex with cyclodextrin in the composition, at the usage concentration, so that an effective amount of both the free, uncomplexed active and free, uncomplexed cyclodextrin are available for their intended use. Furthermore, it is desirable to include a humectant to maintain a desirable moisture level in cotton fabrics while they dry to maximize dewrinkling.

SUMMARY OF THE INVENTION

The present invention relates to a stable, preferably translucent, more preferably clear, aqueous odor-absorbing and wrinkle controlling composition, odor control and wrinkle control methods and articles of manufacture that use such odor-absorbing and wrinkle controlling composition, preferably for use on inanimate surfaces, especially fabrics comprising:

(A). an effective amount to absorb malodors, typically from about 0.01% to about 20% by weight of the composition, with concentrated compositions which are meant to be diluted containing from about 3% to about 20%, preferably from about 5% to about 10% by weight of the composition, and, for more dilute "usage conditions" compositions, a range of from about 0.01% to about 5%, preferably from about 0.1% to about 3%, more preferably from about 0.5% to about 2%, by weight of the usage composition, of solubilized, uncomplexed cyclodextrin;

(B). optionally, an effective amount to improve the performance of the composition, preferably from about 0.05% to about 5%, more preferably from about 0.1% to about 3%, and even more preferably from about 0.2% to about 1.5%, by weight of the usage composition, of cyclodextrin compatible surfactant that preferably provides a surface tension of from about 20 dyne/cm to about 60 dyne/cm, preferably from about 20 dyne/cm to about 45 dyne/cm (with concentrated compositions having a level of from about 0.1% to about 15%, preferably from about 0.2% to about 8%, more preferably from about 0.3% to about 5%, by weight of the concentrated solution, of cyclodextrin-compatible surfactant);

(C). optionally, an effective amount, to kill, or reduce the growth of microbes, of cyclodextrin compatible and water soluble antimicrobial active, preferably from about 0.001% to about 0.8%, more preferably from about 0.002% to about 0.3%, even more preferably from about 0.003% to about 0.2%, by weight of the usage composition, and preferably selected from the group consisting of halogenated compounds, cyclic nitrogen compounds, quaternary compounds, and phenolic compounds (with concentrated compositions having a level of from about 0.003% to about 2%, preferably from about 0.01% to about 1.2%, more preferably from about 0.1% to about 0.8%, by weight of the concentrated solution, of cyclodextrin-compatible and water soluble antimicrobial active);

(D). optionally, but preferably, an effective amount to provide olfactory effects of perfume, typically from about 0.003% to about 0.5%, preferably from about 0.01% to about 0.3%, more preferably from about 0.05% to about 0.2%, by weight of the usage composition of hydrophilic perfume, containing at least about 50%, preferably at least about 60%, more preferably at least about 60%, even more preferably at least about 70%, and yet more preferably at least about 80%, by weight of the perfume of perfume ingredients that have a ClogP of less than about 3.5 and optionally, a minor amount of perfume ingredients selected from the group consisting of ambrox, bacdanol, benzyl salicylate, butyl anthranilate, cetalox, damascenone, alpha-damascone, gamma-dodecalactone, ebanol, herbavert, cis-3-hexenyl salicylate, alpha-ionone, beta-ionone, alpha-isomethylionone, lilial, methyl nonyl ketone, gamma-undecalactone, undecylenic aldehyde, and mixtures thereof;

(E). optionally, but preferably, from about 0.01% to about 3%, more preferably from about 0.05% to about 1%, and even more preferably from about 0.1% to about 0.5%, by weight of the usage composition of low molecular weight polyol;

(F). optionally, an effective amount to assist in antimicrobial action of aminocarboxylate chelator; preferably from about 0.001% to about 0.3%, preferably from about 0.01% to about 0.1%, more preferably from about 0.02% to about 0.05%, by weight of the usage composition;

(G). optionally, but preferably, an effective amount of metallic salt, preferably from about 0.1% to about 10%, more preferably from about 0.2% to about 8%, even more preferably from about 0.3% to about 5% by weight of the usage composition, especially water soluble copper and/or zinc salts, for improved odor benefit;

(H). optionally, an effective amount of enzyme, from about 0.0001% to about 0.5%, preferably from about 0.001% to about 0.3%, more preferably from about 0.005% to about 0.2% by weight of the usage composition, for improved odor control benefit;

(I). optionally, an effective amount of solubilized, water-soluble, antimicrobial preservative, preferably from about 0.0001% to about 0.5%, more preferably from about 0.0002% to about 0.2%, most preferably from about 0.0003% to about 0.1%, by weight of the composition;

(J). an effective amount of cyclodextrin compatible fabric wrinkle control agent, preferably from about 0.05% to about 5%, more preferably from about 0.2% to about 3%, even more preferably from about 0.3% to about 2%, by weight of the usage composition; and (K). aqueous carrier, said composition preferably containing at least one of (B) and (C) and preferably being essentially free of any material that would soil or stain fabric under usage conditions, and/or preferably having a pH of more than about 3, more preferably more than about 3.5.

The present invention also relates to concentrated compositions, wherein the level of cyclodextrin is from about 3% to about 20%, more preferably from about 5% to about 10%, by weight of the composition which are diluted to form compositions with the usage concentrations of cyclodextrin of, e.g., from about 0.1% to about 5%, by weight of the diluted composition, as given hereinabove, which are the "usage conditions".

The present invention also relates to the compositions incorporated into a spray dispenser to create an article of manufacture that can facilitate treatment of articles and/or surfaces with said compositions containing uncomplexed cyclodextrin and other optional ingredients at a level that is effective, yet is not discernible when dried on the surfaces. The spray dispenser comprises manually activated and non-manual operated spray means and a container containing the odor-absorbing composition.

The present invention also comprises the use of small particle diameter droplets of the compositions herein, even those which do not contain (B) or (C), to treat surfaces, especially fabrics, to provide superior performance, e.g., the method of applying the compositions to fabrics, etc. as very small particles (droplets) preferably having average particle sizes (diameters) of from about 10 $\mu$m to about 120 $\mu$m, more preferably from about 20 $\mu$m to about 100 $\mu$m.

In another aspect of the invention herein, compositions that contain combinations of water soluble antimicrobial actives, especially those described hereinafter, and especially the bis-biguanide alkane compounds described hereinafter, and the surfactants described hereinafter, especially the polyalkylene oxide polysiloxanes described hereinafter provide superior antimicrobial action in aqueous solutions, either by themselves, or in combination with the other ingredients, including the cyclodextrin.

DETAILED DESCRIPTION OF THE INVENTION

The present invention relates to a stable, preferably translucent, more preferably clear, aqueous odor-absorbing and wrinkle controlling composition, odor control and wrinkle control methods and articles of manufacture that use such odor-absorbing and wrinkle controlling composition, preferably for use on fabrics, comprising:

(A). an effective amount to absorb malodors, typically from about 0.01% to about 20% by weight of the composition, with concentrated compositions which are meant to be diluted containing from about 3% to about 20%, preferably from about 5% to about 10% by weight of the composition, and, for more dilute "usage conditions" compositions, a range of from about 0.01% to about 5%, preferably from about 0.1% to about 3%, more preferably from about 0.5% to about 2%, by weight of the usage composition, of solubilized, uncomplexed cyclodextrin;

(B). optionally, an effective amount to improve the performance of the composition, preferably from about 0.05% to about 5%, more preferably from about 0.1% to about 3%, and even more preferably from about 0.2% to about 1.5%, by weight of the usage composition, of cyclodextrin compatible surfactant that preferably provides a surface tension of from about 20 dyne/cm to about 60 dyne/cm, preferably from about 20 dyne/cm to about 45 dyne/cm (with concentrated compositions having a level of from about 0.1% to about 8%, preferably from about 0.2% to about 4%, more preferably from about 0.3% to about 3%, by weight of the concentrated solution, of cyclodextrin-compatible surfactant);

(C). optionally, an effective amount, to kill, or reduce the growth of microbes, of cyclodextrin compatible and water soluble antimicrobial active, preferably from about 0.001% to about 0.8%, more preferably from about 0.002% to about 0.3%, even more preferably from about 0.003% to about 0.2%, by weight of the usage composition, and preferably selected from the group consisting of halogenated compounds, cyclic nitrogen compounds, quaternary compounds, and phenolic compounds (with concentrated compositions having a level of from about 0.003% to about 2%, preferably from about 0.01% to about 1.2%, more preferably from about 0.1% to about 0.8%, by weight of the concentrated solution, of cyclodextrin-compatible and water soluble antimicrobial active);

(D). optionally, but preferably, an effective amount to improve acceptance of the composition, typically from about 0.003% to about 0.5%, preferably from about 0.01% to about 0.3%, more preferably from about 0.05% to about 0.2%, by weight of the usage composition of hydrophilic perfume, containing at least about 50%, preferably at least about 60%, more preferably at least about 60%, even more preferably at least about 70%, and yet more preferably at least about 80%, by weight of the perfume of perfume ingredients that have a ClogP of less than about 3.5 and optionally, a minor amount of perfume ingredients selected from the group consisting of ambrox, bacdanol, benzyl salicylate, butyl anthranilate, cetalox, damascenone, alpha-damascone, gamma-dodecalactone, ebanol, herbavert, cis-3-hexenyl salicylate, alpha-ionone, beta-ionone, alpha-isomethylionone, lilial, methyl nonyl ketone, gamma-undecalactone, undecylenic aldehyde, and mixtures thereof;

(E). optionally, but preferably, from about 0.01% to about 3%, more preferably from about 0.05% to about 1%, and even more preferably from about 0.1% to about 0.5%, by weight of the usage composition of low molecular weight polyol;

(F). optionally, an effective amount to assist in antimicrobial action of aminocarboxylate chelator, preferably from about 0.001% to about 0.3%, preferably from about 0.01% to about 0.1%, more preferably from about 0.02% to about 0.05%, by weight of the usage composition;

(G). optionally, but preferably, an effective amount of metallic salt, preferably from about 0.1% to about 10%, more preferably from about 0.2% to about 8%, even more preferably from about 0.3% to about 5% by weight of the usage composition, especially water soluble copper and/or zinc salts, for improved odor benefit;

(H). optionally, an effective amount of enzyme, from about 0.0001% to about 0.5%, preferably from about 0.001% to about 0.3%, more preferably from about 0.005% to about 0.2% by weight of the usage composition, for improved odor control benefit;

(I). optionally, an effective amount of solubilized, water-soluble, antimicrobial preservative, preferably from about 0.0001% to about 0.5%, more preferably from about 0.0002% to about 0.2%, most preferably from about 0.0003% to about 0.1%, by weight of the composition;

(J). an effective amount of cyclodextrin compatible fabric wrinkle control agent, preferably selected from the group consisting of fabric lubricant, shape retention polymer, hydrophilic plasticizer, lithium salts, and mixtures thereof, preferably from about 0.05% to about 5%, more preferably from about 0.2% to about 3%, even more preferably from about 0.3% to about 2% by weight of the usage composition; and (K). aqueous carrier,
said composition preferably containing at least one of (B), and (C), and preferably being essentially free of any material that would soil or stain fabric under usage conditions, and/or preferably having a pH of more than about 3, more preferably more than about 3.5. In the presence of some preferred shape retention polymer, the composition preferably has a pH of from about 6.5 to about 11, more preferably from about 7 to about 10, and even more preferably from about 7 to about 8.

The present invention also relates to the compositions incorporated into a spray dispenser (sprayer) to create an article of manufacture that can facilitate treatment of articles and/or surfaces with said compositions containing uncomplexed cyclodextrin and other optional ingredients at a level that is effective, yet is not discernible when dried on the surfaces. The spray dispenser comprises both manually activated and non-manual operated spray means and a container containing the odor-absorbing composition.

The present invention also relates to concentrated compositions, wherein the level of cyclodextrin is from about 3% to about 20%, preferably from about 4% to about 15%, more preferably from about 5% to about 10%, by weight of the concentrated composition. The concentrated composition is typically diluted to form usage compositions, with the usage concentration of, e.g., from about 0.1% to about 5%, by weight of the usage composition, as given hereinabove. Specific levels of other optional ingredients in the concentrated composition can readily be determined from the desired usage composition and the desired degree of concentration. These concentrated compositions can be used in a process for preparing large volumes of treatment composition in which water is added, either in a separate container, or in the container of the article of manufacture comprising the spray means.

The above compositions for odor control are of the type disclosed in U.S. Pat. Nos. 5,534,165; 5,578,563; 5,663,134; 5,668,097; 5,670,475; and 5,714,137, Trinh et al. issued Jul. 9, 1996; Nov. 26, 1996; Sep. 2, 1997; Sep. 16, 1997; Sep. 23, 1997; and Feb. 3, 1998 respectively, all of said patents being incorporated herein by reference. All of the patents, patent applications, and references referred to herein are incorporated, either wholly, or in relevant part, by reference. All parts, ratios, and percentages herein are by weight and all numerical limits are used with the normal degree of accuracy afforded by the art unless otherwise specified.

I. Composition

(A). Cyclodextrin

As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in donut-shaped rings. The specific coupling and conformation of the glucose units give the cyclodextrins rigid, conical molecular structures with hollow interiors of specific volumes. The "lining" of each internal cavity is formed by hydrogen atoms and glycosidic bridging oxygen atoms; therefore, this surface is fairly hydrophobic. The unique shape and physical-chemical properties of the cavity enable the cyclodextrin molecules to absorb (form inclusion complexes with) organic molecules or parts of organic molecules which can fit into the cavity. Many odorous molecules can fit into the cavity including many malodorous molecules and perfume molecules. Therefore, cyclodextrins, and especially mixtures of cyclodextrins with different size cavities, can be used to control odors caused by a broad spectrum of organic odoriferous materials, which may, or may not, contain reactive functional groups. The complexation between cyclodextrin and odorous molecules occurs rapidly in the presence of water. However, the extent of the complex formation also depends on the polarity of the absorbed molecules. In an aqueous solution, strongly hydrophilic molecules (those which are highly water-soluble) are only partially absorbed, if at all. Therefore, cyclodextrin does not complex effectively with some very low molecular weight organic amines and acids when they are present at low levels on wet fabrics. As the water is being removed however, e.g., the fabric is being dried off, some low molecular weight organic amines and acids have more affinity and will complex with the cyclodextrins more readily.

The cavities within the cyclodextrin in the solution of the present invention should remain essentially unfilled (the cyclodextrin remains uncomplexed) while in solution, in order to allow the cyclodextrin to absorb various odor molecules when the solution is applied to a surface. Non-derivatised (normal) beta-cyclodextrin can be present at a level up to its solubility limit of about 1.85% (about 1.85 g in 100 grams of water) at room temperature. Beta-cyclodextrin is not preferred in compositions which call for a level of cyclodextrin higher than its water solubility limit. Non-derivatised beta-cyclodextrin is generally not preferred when the composition contains surfactant since it affects the surface activity of most of the preferred surfactants that are compatible with the derivatised cyclodextrins.

Preferably, the odor absorbing solution of the present invention is clear. The term "clear" as defined herein means transparent or translucent, preferably transparent, as in "water clear," when observed through a layer having a thickness of less than about 10 cm.

Preferably, the cyclodextrins used in the present invention are highly water-soluble such as, alpha-cyclodextrin and/or derivatives thereof, gamma-cyclodextrin and/or derivatives thereof, derivatised beta-cyclodextrins, and/or mixtures thereof. The derivatives of cyclodextrin consist mainly of molecules wherein some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins, wherein R is a —$CH_2$—CH(OH)—$CH_3$ or a —$CH_2CH_2$—OH group; branched cyclodextrins such as maltose-bonded cyclodextrins; cationic cyclodextrins such as those containing 2-hydroxy-3-(dimethylamino)propyl ether, wherein R is $CH_2$—CH(OH)—$CH_2$—$N(CH_3)_2$ which is cationic at low pH; quaternary ammonium, e.g., 2-hydroxy-3-(trimethylammonio) propyl ether chloride groups, wherein R is $CH_2$—CH(OH)—$CH_2$—$N^+(CH_3)_3Cl^-$; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins, as disclosed in "Optimal Performances with Minimal Chemical Modification of Cyclodextrins", F. Diedaini-Pilard and B. Perly, The 7th International Cyclodextrin Symposium Abstracts, April 1994, p. 49, said references being incorporated herein by reference; and mixtures thereof. Other cyclodextrin derivatives are disclosed in U.S. Pat. Nos: 3.426,011, Parmerter et al., issued Feb. 4, 1969; 3,453,257; 3,453,258; 3,453,259; and 3,453,260, all in the names of Parmerter et al., and all issued Jul. 1, 1969; 3,459,731, Gramera et al., issued Aug. 5, 1969; 3,553,191, Parmerter et al., issued Jan. 5, 1971; 3,565,887, Parmerter et al., issued Feb. 23, 1971; 4,535,152, Szejtli et al., issued Aug. 13, 1985; 4,616,008, Hirai et al., issued Oct. 7, 1986; 4,678,598, Ogino et al., issued Jul. 7, 1987; 4,638,058, Brandt et al., issued Jan. 20, 1987; and 4,746,734, Tsuchiyama et al., issued May 24, 1988; all of said patents being incorporated herein by reference.

Highly water-soluble cyclodextrins are those having water solubility of at least about 10 g in 100 ml of water at room temperature, preferably at least about 20 g in 100 ml of water, more preferably at least about 25 g in 100 ml of water at room temperature. The availability of solubilized, uncomplexed cyclodextrins is essential for effective and efficient odor control performance. Solubilized, water-soluble cyclodextrin can exhibit more efficient odor control performance than non-water-soluble cyclodextrin when deposited onto surfaces, especially fabric.

Examples of preferred water-soluble cyclodextrin derivatives suitable for use herein are hydroxypropyl alpha-cyclodextrin, methylated alpha-cyclodextrin, methylated beta-cyclodextrin, hydroxyethyl beta-cyclodextrin, and hydroxypropyl beta-cyclodextrin. Hydroxyalkyl cyclodextrin derivatives preferably have a degree of substitution of from about 1 to about 14, more preferably from about 1.5 to about 7, wherein the total number of OR groups per cyclodextrin is defined as the degree of substitution. Methylated cyclodextrin derivatives typically have a degree of substitution of from about 1 to about 18, preferably from about 3 to about 16. A known methylated beta-cyclodextrin is heptakis-2,6-di-O-methyl-β-cyclodextrin, commonly known as DIMEB, in which each glucose unit has about 2 methyl groups with a degree of substitution of about 14. A preferred, more commercially available, methylated beta-cyclodextrin is a randomly methylated beta-cyclodextrin, commonly known as RAMEB, having different degrees of substitution, normally of about 12.6. RAMEB is more preferred than DIMEB, since DIMEB affects the surface activity of the preferred surfactants more than RAMEB. The preferred cyclodextrins are available, e.g., from Cerestar USA, Inc. and Wacker Chemicals (USA), Inc.

It is also preferable to use a mixture of cyclodextrins. Such mixtures absorb odors more broadly by complexing with a wider range of odoriferous molecules having a wider range of molecular sizes. Preferably at least a portion of the cyclodextrins is alpha-cyclodextrin and its derivatives thereof, gamma-cyclodextrin and its derivatives thereof, and/or derivatised beta-cyclodextrin, more preferably a mixture of alpha-cyclodextrin, or an alpha-cyclodextrin derivative, and derivatised beta-cyclodextrin, even more preferably a mixture of derivatised alpha-cyclodextrin and derivatised beta-cyclodextrin, most preferably a mixture of hydroxypropyl alpha-cyclodextrin and hydroxypropyl beta-cyclodextrin, and/or a mixture of methylated alpha-cyclodextrin and methylated beta-cyclodextrin.

For controlling odor on fabrics, the composition is preferably used as a spray. It is preferable that the usage compositions of the present invention contain low levels of cyclodextrin so that a visible stain does not appear on the fabric at normal usage levels. Preferably, the solution used to treat the surface under usage conditions is virtually not discernible when dry. Typical levels of cyclodextrin in usage compositions for usage conditions are from about 0.01% to about 5%, preferably from about 0.1% to about 4%, more preferably from about 0.5% to about 2% by weight of the composition. Compositions with higher concentrations can leave unacceptable visible stains on fabrics as the solution evaporates off of the fabric. This is especially a problem on thin, colored, synthetic fabrics. In order to avoid or minimize the occurrence of fabric staining, it is preferable that the fabric be treated at a level of less than about 5 mg of cyclodextrin per gram of fabric, more preferably less than about 2 mg of cyclodextrin per gram of fabric. The presence of the surfactant can improve appearance by minimizing localized spotting.

Concentrated compositions can also be used in order to deliver a less expensive product. When a concentrated product is used, i.e., when the level of cyclodextrin used is from about 3% to about 20%, more preferably from about 5% to about 10%, by weight of the concentrated composition, it is preferable to dilute the concentrated composition before treating fabrics in order to avoid staining. Preferably the concentrated cyclodextrin composition is diluted with about 50% to about 6000%, more preferably with about 75% to about 2000%, most preferably with about 100% to about 1000% by weight of the concentrated composition of water. The resulting diluted compositions have usage concentrations of cyclodextrin as discussed hereinbefore, e.g., of from about 0.1% to about 5%, by weight of the diluted composition.

(B). Cyclodextrin-compatible Surfactant

The cyclodextrin-compatible surfactant B., provides a low surface tension that permits the composition to spread readily and more uniformly on hydrophobic surfaces like polyester and nylon. It has been found that the aqueous solution, without such a surfactant will not spread satisfactorily. The spreading of the composition also allows it to dry faster, so that the treated material is ready to use sooner. Furthermore, the composition containing a cyclodextrin-compatible surfactant can penetrate hydrophobic, oily soil better for improved malodor control. The composition containing a cyclodextrin-compatible surfactant also provides improved "in-wear" electrostatic control. For concentrated compositions, the surfactant facilitates the dispersion of many actives such as antimicrobial actives and perfumes in the concentrated aqueous compositions.

The surfactant is also needed in the composition of the present invention that contains a wrinkle control agent such as silicone and/or shape retention polymer. For such agents, the surfactant is also needed, e.g., as a dispersing agent, an emulsifying agent and/or a solubilizing agent.

The surfactant for use in providing the required low surface tension in the composition of the present invention should be cyclodextrin-compatible, that is it should not substantially form a complex with the cyclodextrin so as to diminish performance of the cyclodextrin and/or the surfactant. Complex formation diminishes both the ability of the cyclodextrin to absorb odors and the ability of the surfactant to lower the surface tension of the aqueous composition.

Suitable cyclodextrin-compatible surfactants can be readily identified by the absence of effect of cyclodextrin on the surface tension provided by the surfactant. This is achieved by determining the surface tension (in dyne/cm$^2$) of aqueous solutions of the surfactant in the presence and in the absence of about 1% of a specific cyclodextrin in the solutions. The aqueous solutions contain surfactant at concentrations of approximately 0.5%, 0.1%, 0.01%, and 0.005%. The cyclodextrin can affect the surface activity of a surfactant by elevating the surface tension of the surfactant solution. If the surface tension at a given concentration in water differs by more than about 10% from the surface tension of the same surfactant in the 1% solution of the cyclodextrin, that is an indication of a strong interaction between the surfactant and the cyclodextrin. The preferred surfactants herein should have a surface tension in an aqueous solution that is different (lower) by less than about 10%, preferably less than about 5%, and more preferably less than about 1% from that of the same concentration solution containing 1% cyclodextrin.

Nonlimiting examples of cyclodextrin-compatible nonionic surfactants include block copolymers of ethylene oxide and propylene oxide. Suitable block polyoxyethylene-polyoxypropylene polymeric surfactants, that are compatible with most cyclodextrins, include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as $C_{12-18}$ aliphatic alcohols, are not generally compatible with the cyclodextrin. Certain of the block polymer surfactant compounds designated Pluronic® and Tetronic® by the BASF-Wyandotte Corp., Wyandotte, Mich., are readily available.

Nonlimiting examples of cyclodextrin-compatible surfactants of this type include:

Pluronic Surfactants with the general formula $H(EO)_n(PO)_m(EO)_nH$, wherein EO is an ethylene oxide group, PO is a propylene oxide group, and n and m are numbers that indicate the average number of the groups in the surfactants. Typical examples of cyclodextrin-compatible Pluronic surfactants are:

| Name  | Average MW | Average n | Average m |
|-------|------------|-----------|-----------|
| L-101 | 3,800      | 4         | 59        |
| L-81  | 2,750      | 3         | 42        |
| L-44  | 2,200      | 10        | 23        |
| L-43  | 1,850      | 6         | 22        |
| F-38  | 4,700      | 43        | 16        |
| P-84  | 4,200      | 19        | 43,       | and mixtures thereof.

Tetronic Surfactants with the general formula:

wherein EO, PO, n, and m have the same meanings as above. Typical examples of cyclodextrin-compatible Tetronic surfactants are:

| Name | Average MW | Average n | Average m |
|------|------------|-----------|-----------|
| 901  | 4,700      | 3         | 18        |
| 908  | 25,000     | 114       | 22,       | and mixtures thereof.

"Reverse" Pluronic and Tetronic surfactants have the following general formulas:

Reverse Pluronic Surfactants $H(PO)_m(EO)_n(PO)_mH$

Reverse Tetronic Surfactants

wherein EO, PO, n, and m have the same meanings as above. Typical examples of cyclodextrin-compatible Reverse Pluronic and Reverse Tetronic surfactants are:

| Name | Average MW | Average n | Average m |
|---|---|---|---|
| Reverse Pluronic surfactants: | | | |
| 10 R5 | 1,950 | 8 | 22 |
| 25 R1 | 2,700 | 21 | 6 |
| Reverse Tetronic surfactants | | | |
| 130 R2 | 7,740 | 9 | 26 |
| 70 R2 | 3,870 | 4 | 13 | and mixtures thereof.

A preferred class of cyclodextrin-compatible nonionic surfactants are the polyalkylene oxide polysiloxanes having a dimethyl polysiloxane hydrophobic moiety and one or more hydrophilic polyalkylene side chains, and having the general formula:

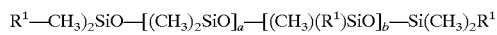

wherein a +b are from about 1 to about 50, preferably from about 3 to about 30, more preferably from about 10 to about 25, and each $R^1$ is the same or different and is selected from the group consisting of methyl and a poly(ethyleneoxide/propyleneoxide) copolymer group having the general formula:

$$-(CH_2)_nO(C_2H_4O)_c(C_3H_6O)_dR^2$$

with at least one $R^1$ being a poly(ethyleneoxide/propyleneoxide) copolymer group, and wherein n is 3 or 4, preferably 3; total c (for all polyalkyleneoxy side groups) has a value of from 1 to about 100, preferably from about 6 to about 100; total d is from 0 to about 14, preferably from 0 to about 3; and more preferably d is 0; total c+d has a value of from about 5 to about 150, preferably from about 9 to about 100 and each $R^2$ is the same or different and is selected from the group consisting of hydrogen, an alkyl having 1 to 4 carbon atoms, and an acetyl group, preferably hydrogen and methyl group. Each polyalkylene oxide polysiloxane has at least one $R^1$ group being a poly(ethyleneoxide/propyleneoxide) copolymer group.

Nonlimiting examples of this type of surfactants are the Silwet® surfactants which are available OSi Specialties, Inc., Danbury, Conn. Representative Silwet surfactants are as follows.

| Name | Average MW | Average a + b | Average total c |
|---|---|---|---|
| L-7608 | 609 | 1 | 9 |
| L-7607 | 1,00 | 2 | 17 |
| L-77 | 600 | 1 | 9 |
| L-7605 | 6,000 | 20 | 99 |
| L-7604 | 4,000 | 21 | 53 |
| L-7600 | 4,000 | 11 | 68 |
| L-7657 | 5,000 | 20 | 76 |
| L-7602 | 3,000 | 20 | 29 |

The molecular weight of the polyalkyleneoxy group ($R^1$) is less than or equal to about 10,000. Preferably, the molecular weight of the polyalkyleneoxy group is less than or equal to about 8,000, and most preferably ranges from about 300 to about 5,000. Thus, the values of c and d can be those numbers which provide molecular weights within these ranges. However, the number of ethyleneoxy units ($-C_2H_4O$) in the polyether chain ($R^1$) must be sufficient to render the polyalkylene oxide polysiloxane water dispersible or water soluble. If propyleneoxy groups are present in the polyalkylenoxy chain, they can be distributed randomly in the chain or exist as blocks. Preferred Silwet surfactants are L-7600, L-7602, L-7604, L-7605, L-7622, L-7657, and mixtures thereof. Besides surface activity, polyalkylene oxide polysiloxane surfactants can also provide other benefits, such as antistatic benefits, lubricity and softness to fabrics.

The preparation of polyalkylene oxide polysiloxanes is well known in the art. Polyalkylene oxide polysiloxanes of the present invention can be prepared according to the procedure set forth in U.S. Pat. No. 3,299,112, incorporated herein by reference. Typically, polyalkylene oxide polysiloxanes of the surfactant blend of the present invention are readily prepared by an addition reaction between a hydrosiloxane (i.e., a siloxane containing silicon-bonded hydrogen) and an alkenyl ether (e.g., a vinyl, allyl, or methallyl ether) of an alkoxy or hydroxy end-blocked polyalkylene oxide). The reaction conditions employed in addition reactions of this type are well known in the art and in general involve heating the reactants (e.g., at a temperature of from about 85° C. to 110° C.) in the presence of a platinum catalyst (e.g., chloroplatinic acid) and a solvent (e.g., toluene).

Nonlimiting examples of cyclodextrin-compatible anionic surfactants are the alkyldiphenyl oxide disulfonate, having the general formula:

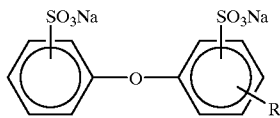

wherein R is an alkyl group. Examples of this type of surfactants are available from the Dow Chemical Company under the trade name Dowfax® wherein R is a linear or branched $C_6-C_{16}$ alkyl group. An example of these cyclodextrin-compatible anionic surfactant is Dowfax 3B2 with R being approximately a linear $C_{10}$ group. These anionic surfactants are preferably not used when the antimicrobial active or preservative, etc., is cationic to minimize the interaction with the cationic actives, since the effect of both surfactant and active are diminished.

The surfactants above are either weakly interactive with cyclodextrin (less than 5% elevation in surface tension, or non-interactive (less than 1% elevation in surface tension). Normal surfactants like sodium dodecyl sulfate and dodecanolpoly(6)ethoxylate are strongly interactive, with more than a 10% elevation in surface tension in the presence of a typical cyclodextrin like hydroxypropyl-beta-cyclodextrin and methylated beta-cyclodextrin.

Typical levels of cyclodextrin-compatible surfactants in usage compositions are from about 0.01% to about 2%, preferably from about 0.03% to about 0.6%, more preferably from about 0.05% to about 0.3%, by weight of the composition. Typical levels of cyclodextrin-compatible surfactants in concentrated compositions are from about 0.1% to about 8%. preferably from about 0.2% to about 4%, more preferably from about 0.3% to about 3%, by weight of the concentrated composition. For composition containing wrinkle control agent, typical levels of cyclodextrin-compatible surfactants in the usage compositions are from about 0.05% to about 5%, preferably from about 0.1% to about 3%, more preferably from about 0.2% to about 1.5%, by weight of the composition.

(C). Cyclodextrin-compatible Antimicrobial Active

The solubilized, water-soluble antimicrobial active, C., is useful in providing protection against organisms that become attached to the treated material. The antimicrobial should be cyclodextrin-compatible, e.g., not substantially forming complexes with the cyclodextrin in the odor absorbing composition. The free, uncomplexed antimicrobial, e.g., antibacterial, active provides an optimum antibacterial performance.

Sanitization of fabrics can be achieved by the compositions of the present invention containing, antimicrobial materials, e.g., antibacterial halogenated compounds, quaternary compounds, and phenolic compounds.

Biguanides. Some of the more robust cyclodextrin-compatible antimicrobial halogenated compounds which can function as disinfectants/sanitizers as well as finish product preservatives (vide infra), and are useful in the compositions of the present invention include 1,1'-hexamethylene bis(5-(p-chlorophenyl)biguanide), commonly known as chlorhexidine, and its salts, e.g., with hydrochloric, acetic and gluconic acids. The digluconate salt is highly water-soluble, about 70% in water, and the diacetate salt has a solubility of about 1.8% in water. When chlorhexidine is used as a sanitizer in the present invention it is typically present at a level of from about 0.001% to about 0.4%, preferably from about 0.002% to about 0.3%, and more preferably from about 0.05% to about 0.2%, by weight of the usage composition. In some cases, a level of from about 1% to about 2% may be needed for virucidal activity.

Other useful biguanide compounds include Cosmoci® CQ®, Vantocil® IB, including poly (hexamethylene biguanide) hydrochloride. Other useful cationic antimicrobial agents include the bis-biguanide alkanes. Usable water soluble salts of the above are chlorides, bromides, sulfates, alkyl sulfonates such as methyl sulfonate and ethyl sulfonate, phenylsulfonates such as p-methylphenyl sulfonates, nitrates, acetates, gluconates, and the like.

Examples of suitable bis biguanide compounds are chlorhexidine; 1,6-bis-(2-ethylhexylbiguanidohexane) dihydrochloride; 1,6-di-($N_1,N_1$'-phenyldiguanido-$N_5,N_5$')-hexane tetrahydrochloride; 1,6-di-($N_1,N_1$'-phenyl-$N_1,N_1$'-methyldiguanido-$N_5,N_5$')-hexane dihydrochloride; 1,6-di ($N_1,N_1$'-o-chlorophenyldiguanido-$N_5,N_5$')-hexane dihydrochloride; 1,6-di($N_1,N_1$'-2,6-dichlorophenyldiguanido-$N_5,N_5$')hexane dihydrochloride; 1,6-di[$N_1,N_1$'-.beta.-(p-methoxyphenyl) diguanido-$N_5,N_5$']-hexane dihydrochloride; 1,6-di($N_1,N_1$'-.alpha.-methyl-.beta.-phenyldiguanido-$N_5N_5$')-hexane dihydrochloride; 1,6-di($N_1,N_1$'-p-nitrophenyldiguanido-$N_5,N_5$')hexane dihydrochloride;.omega.:.omega.'-di-($N_1,N_1$'-phenyldiguanido-$N_5,N_5$')-di-n-propylether dihydrochloride;.omega:omega'-di($N_1,N_1$'-p-chlorophenyldiguanido-$N_5$, $N_5$')-di-n-propylether tetrahydrochloride; 1,6-di($N_1,N_1$'-2,4-dichlorophenyldiguanido-$N_5$, $N_5$')hexane tetrahydrochloride; 1,6-di(N $_1$,N$_1$'-p-methylphenyldiguanido-$N_5,N_5$')hexane dihydrochloride; 1,6-di($N_1,N_1$'-2,4,5-trichlorophenyldiguanido-$N_5,N_5$') hexane tetrahydrochloride; 1,6-di[$N_1,N_1$'-.alpha.-(p-chlorophenyl) ethyldiguanido-$N_5,N_5$'] hexane dihydrochloride;.omega.:.omega.'di($N_1$, $N_1$'-p-chlorophenyldiguanido-$N_5,N_5$')m-xylene dihydrochloride; 1,12-di($N_1,N_1$'-p-chlorophenyldiguanido-$N_5,N_5$') dodecane dihydrochloride; 1,10-di($N_1,N_1$'-phenyldiguanido-$N_5,N_5$')-decane tetrahydrochloride; 1,12-di($N_1,N_1$'-phenyldiguanido-$N_5,N_5$') dodecane tetrahydrochloride; 1,6-di($N_1,N_1$'-o-chlorophenyldiguanido-$N_5,N_5$') hexane dihydrochloride; 1,6-di($N_1,N_1$'-p-chlorophenyldiguanido-$N_5,N_5$')-hexane tetrahydrochloride; ethylene bis (1-tolyl biguanide); ethylene bis (p-tolyl biguanide); ethylene bis(3, 5-dimethylphenyl biguanide); ethylene bis(p-tert-amylphenyl biguanide); ethylene bis(nonylphenyl biguanide); ethylene bis (phenyl biguanide); ethylene bis (N-butylphenyl biguanide); ethylene bis (2,5-diethoxyphenyl biguanide); ethylene bis(2,4-dimethylphenyl biguanide); ethylene bis(o-diphenylbiguanide); ethylene bis(mixed amyl naphthyl biguanide); N-butyl ethylene bis(phenylbiguanide); trimethylene bis(o-tolyl biguanide); N-butyl trimethylene bis (phenyl biguanide); and the corresponding pharmaceutically acceptable salts of all of the above such as the acetates; gluconates; hydrochlorides; hydrobromides; citrates; bisulfites; fluorides; polymaleates; N-coconutalkylsarcosinates; phosphites; hypophosphites; perfluorooctanoates; silicates; sorbates; salicylates; maleates; tartrates; fumarates; ethylenediaminetetraacetates; iminodiacetates; cinnamates; thiocyanates; arginates; pyromellitates; tetracarboxybutyrates; benzoates; glutarates; monofluorophosphates; and perfluoropropionates, and mixtures thereof. Preferred antimicrobials from this group are 1,6-di-($N_1,N_1$'-phenyldiguanido-$N_5,N_5$')-hexane tetrahydrochloride; 1,6-di($N_1,N_1$'-o-chlorophenyldiguanido-$N_5,N_5$')-hexane dihydrochloride; 1,6-di($N_1,N_1$'-2,6-dichlorophenyldiguanido-$N_5,N_5$')hexane dihydrochloride; 1,6-di($N_1,N_1$'-2,4-dichlorophenyldiguanido-$N_5,N_5$')hexane tetrahydrochloride; 1,6-di[$N_1,N_1$'-.alpha.-(p-chlorophenyl) ethyldiguanido-$N_5,N_5$'] hexane dihydrochloride;.omega.:.omega.'di($N_1,N_1$'-p-chlorophenyldiguanido-$N_5,N_5$')m-xylene dihydrochloride; 1,12-di($N_1,N_1$'-p-chlorophenyldiguanido-$N_5,N_5$') dodecane dihydrochloride; 1,6-di($N_1,N_1$'-o-chlorophenyldiguanido-$N_5,N_5$') hexane dihydrochloride; 1,6-di($N_1,N_1$'-p-chlorophenyldiguanido-$N_5,N_5$')-hexane tetrahydrochloride; and mixtures thereof; more preferably, 1,6-di($N_1,N_1$'-o-chlorophenyldiguanido-$N_5,N_5$')-hexane dihydrochloride; 1,6-di($N_1,N_1$'-2,6-dichlorophenyldiguanido-$N_5,N_5$')hexane dihydrochloride; 1,6-di($N_1,N_1$'-2,4-dichlorophenyldiguanido-$N_5,N_5$')hexane tetrahydrochloride; 1,6-di[$N_1,N_1$'-.alpha.-(p-chlorophenyl) ethyldiguanido-$N_5,N_5$'] hexane dihydrochloride, .omega.:.omega.'di($N_1,N_1$'-p-chlorophenyldiguanido-$N_5$, $N_5$')m-xylene dihydrochloride; 1,12-di($N_1,N_1$'-p-chlorophenyldiguanido-$N_5,N_5$') dodecane dihydrochloride; 1,6-di($N_1,N_1$'-o-chlorophenyldiguanido-$N_5,N_5$') hexane dihydrochloride; 1,6-di($N_1,N_1$'-p-chlorophenyldiguanido-$N_5,N_5$')-hexane tetrahydrochloride; and mixtures thereof. As stated hereinbefore, the bis biguanide of choice is chlorhexidine its salts, e.g., digluconate, dihydrochloride, diacetate, and mixtures thereof.

Quaternary Compounds. A wide range of quaternary compounds can also be used as antimicrobial actives, in conjunction with the preferred surfactants, for compositions of the present invention that do not contain cyclodextrin. Non-limiting examples of useful quaternary compounds include: (1) benzalkonium chlorides and/or substituted benzalkonium chlorides such as commercially available Barquat® (available from Lonza), Maquat® (available from Mason), Variquat® (available from Witco/Sherex), and Hyamine® (available from Lonza); (2) di($C_6$–$C_{14}$)alkyl di short chain ($C_{1-4}$ alkyl and/or hydroxyalkyl) quaternary such as Bardac® products of Lonza, (3) N-(3-chloroallyl) hexaminium chlorides such as Dowicide® and Dowicil® available from Dow; (4) benzethonium chloride such as Hyamine® 1622 from Rohm & Haas; (5) methylbenzethonium chloride represented by Hyamine® 10X supplied by Rohm & Haas, (6) cetylpyridinium chloride available from of Merrell Labs. Examples of the preferred dialkyl quaternary compounds are di($C_8$–$C_{12}$)dialkyl dimethyl ammonium chloride, such as didecyldimethylammonium chloride (Bardac 22), and dioctyldimethylammonium chloride (Bardac 2050). Typical concentrations for biocidal effectiveness of these quaternary compounds range from about 0.001% to about 0.8%, preferably from about 0.005% to about 0.3%, more preferably from about 0.01% to about 0.2%, and even more preferably from about 0.03% to about 0.1%, by weight of the usage composition. The corresponding concentrations for the concentrated compositions are from about 0.003% to about 2%, preferably from about 0.006% to about 1.2%, and more preferably from about 0.1% to about 0.8% by weight of the concentrated compositions.

The surfactants, when added to the antimicrobials tend to provide improved antimicrobial action. This is especially true for the siloxane surfactants, and especially when the siloxane surfactants are combined with the chlorhexidine antimicrobial actives.

(D). Perfume

The odor absorbing composition of the present invention can also optionally provide a "scent signal" in the form of a pleasant odor which signals the removal of malodor from fabrics. The scent signal is designed to provide a fleeting perfume scent, and is not designed to be overwhelming or to be used as an odor masking ingredient. When perfume is added as a scent signal, it is added only at very low levels, e.g., from about 0% to about 0.5%, preferably from about 0.003% to about 0.3%, more preferably from about 0.005% to about 0.2%, by weight of the usage composition.

Perfume can also be added as a more intense odor in product and on surfaces. When stronger levels of perfume are preferred, relatively higher levels of perfume can be added. Any type of perfume can be incorporated into the composition of the present invention. It is essential, however, that the perfume be added at a level wherein even if all of the perfume in the composition were to complex with the cyclodextrin molecules, there will still be an effective level of uncomplexed cyclodextrin molecules present in the solution to provide adequate odor control. In order to reserve an effective amount of cyclodextrin molecules for odor control, perfume is typically present at a level wherein less than about 90% of the cyclodextrin complexes with the perfume, preferably less than about 50% of the cyclodextrin complexes with the perfume, more preferably, less than about 30% of the cyclodextrin complexes with the perfume, and most preferably, less than about 10% of the cyclodextrin complexes with the perfume. The cyclodextrin to perfume weight ratio should be greater than about 8:1, preferably greater than about 10:1, more preferably greater than about 20:1, even more preferably greater than about 40:1 and most preferably greater than about 70:1.

Preferably the perfume is hydrophilic and is composed predominantly of ingredients selected from two groups of ingredients, namely, (a) hydrophilic ingredients having a ClogP of less than about 3.5, more preferably less than about 3.0, and (b) ingredients having significant low detection threshold, and mixtures thereof. Typically, at least about 50%, preferably at least about 60%, more preferably at least about 70%, and most preferably at least about 80% by weight of the perfume is composed of perfume ingredients of the above groups (a) and (b). For these preferred perfumes, the cyclodextrin to perfume weight ratio is typically of from about 2:1 to about 200:1; preferably from about 4:1 to about 100:1, more preferably from about 6:1 to about 50:1, and even more preferably from about 8:1 to about 30:1.

(a). Hydrophilic Perfume Ingredients

The hydrophilic perfume ingredients are more soluble in water, have less of a tendency to complex with the cyclodextrins, and are more available in the odor absorbing composition than the ingredients of conventional perfumes. The degree of hydrophobicity of a perfume ingredient can be correlated with its octanol/water partition coefficient P. The octanol/water partition coefficient of a perfume ingredient is the ratio between its equilibrium concentration in octanol and in water. A perfume ingredient with a greater partition coefficient P is considered to be more hydrophobic. Conversely, a perfume ingredient with a smaller partition coefficient P is considered to be more hydrophilic. Since the partition coefficients of the perfume ingredients normally have high values, they are more conveniently given in the form of their logarithm to the base 10, logP. Thus the preferred perfume hydrophilic perfume ingredients of this invention have logP of about 3.5 or smaller, preferably of about 3.0 or smaller.

The logP of many perfume ingredients have been reported; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The ClogP values, which are the most reliable and widely used estimates for this physicochemical property, are used instead of the experimental logP values in the selection of perfume ingredients which are useful in the present invention.

Non-limiting examples of the more preferred hydrophilic perfume ingredients are allyl amyl glycolate, allyl caproate, amyl acetate, amyl propionate, anisic aldehyde, anisyl acetate, anisole, benzaldehyde, benzyl acetate, benzyl acetone, benzyl alcohol, benzyl formate, benzyl iso valerate, benzyl propionate, beta gamma hexenol, calone, camphor gum, laevo-carveol, d-carvone, laevo-carvone, cinnamic alcohol, cinnamyl acetate, cinnamic alcohol, cinnamyl formate, cinnamyl propionate, cis-jasmone, cis-3-hexenyl acetate, coumarin, cuminic alcohol, cuminic aldehyde, Cyclal C, cyclogalbanate, dihydroeuginol, dihydro isojasmonate, dimethyl benzyl carbinol, dimethyl benzyl carbinyl acetate, ethyl acetate, ethyl aceto acetate, ethyl amyl ketone, ethyl anthranilate, ethyl benzoate, ethyl butyrate, ethyl cinnamate, ethyl hexyl ketone, ethyl maltol, ethyl-2-methyl butyrate, ethyl methylphenyl glycidate, ethyl phenyl acetate, ethyl salicylate, ethyl vanillin, eucalyptol, eugenol, eugenyl acetate, eugenyl formate, eugenyl methyl ether, fenchyl alcohol, flor acetate (tricyclo decenyl acetate), fructone, frutene (tricyclo decenyl propionate), geraniol, geranyl oxyacetaldehyde, heliotropin, hexenol, hexenyl acetate, hexyl acetate, hexyl formate, hinokitiol, hydratropic alcohol, hydroxycitronellal, hydroxycitronellal diethyl acetal, hydroxycitronellol, indole, isoamyl alcohol, iso cyclo citral, isoeugenol, isoeugenyl acetate, isomenthone, isopulegyl acetate, isoquinoline, keone, ligustral, linalool, linalool oxide, linalyl formate, lyral, menthone, methyl acetophenone, methyl amyl ketone, methyl anthranilate, methyl benzoate, methyl benzyl acetate, methyl cinnamate, methyl dihydrojasmonate, methyl eugenol, methyl heptenone, methyl heptine carbonate, methyl heptyl ketone, methyl hexyl ketone, methyl isobutenyl tetrahydropyran, methyl-N-methyl anthranilate, methyl beta naphthyl ketone, methyl phenyl carbinyl acetate, methyl salicylate, nerol, nonalactone, octalactone, octyl alcohol (octanol-2), para-anisic aldehyde, para-cresol, para-cresyl methyl ether, para hydroxy phenyl butanone, para-methoxy acetophenone, para-methyl acetophenone, phenoxy ethanol, phenoxyethyl propionate, phenyl acetaldehyde, phenylacetaldehyde diethyl ether, phenylethyl oxyacetaldehyde, phenyl ethyl acetate, phenyl ethyl alcohol, phenyl ethyl dimethyl carbinol, prenyl acetate, propyl butyrate, pulegone, rose oxide, safrole, terpineol, vanillin, viridine, and mixtures thereof.

Nonlimiting examples of other preferred hydrophilic perfume ingredients which can be used in perfume compositions of this invention are allyl heptoate, amyl benzoate, anethole, benzophenone, carvacrol, citral, citronellol, citronellyl nitrile, cyclohexyl ethyl acetate, cymal, 4-decenal, dihydro isojasmonate, dihydro myrcenol, ethyl methyl phenyl glycidate, fenchyl acetate, florhydral, gamma-nonalactone, geranyl formate, geranyl nitrile, hexenyl isobutyrate, alpha-ionone, isobornyl acetate, isobutyl benzoate, isononyl alcohol, isomenthol, para-isopropyl phenylacetaldehyde, isopulegol, linalyl acetate, 2-methoxy naphthalene, menthyl acetate, methyl chavicol, musk ketone, beta naphthol methyl ether, neral, nonyl aldehyde, phenyl heptanol, phenyl hexanol, terpinyl acetate, Veratrol, yara-yara, and mixtures thereof.

The preferred perfume compositions used in the present invention contain at least 4 different hydrophilic perfume ingredients, preferably at least 5 different hydrophilic perfume ingredients, more preferably at least 6 different hydrophilic perfume ingredients, and even more preferably at least 7 different hydrophilic perfume ingredients. Most common perfume ingredients which are derived from natural sources are composed of a multitude of components. When each such material is used in the formulation of the preferred perfume compositions of the present invention, it is counted as one single ingredient, for the purpose of defining the invention.

(b). Low Odor Detection Threshold Perfume Ingredient

The odor detection threshold of an odorous material is the lowest vapor concentration of that material which can be olfactorily detected. The odor detection threshold and some odor detection threshold values are discussed in, e.g., "Standardized Human Olfactory Thresholds", M. Devos et al, IRL Press at Oxford University Press, 1990, and "Compilation of Odor and Taste Threshold Values Data", F. A. Fazzalari, editor, ASTM Data Series DS 48A, American Society for Testing and Materials, 1978, both of said publications being incorporated by reference. The use of small amounts of perfume ingredients that have low odor detection threshold values can improve perfume odor character, even though they are not as hydrophilic as perfume ingredients of group (a) which are given hereinabove. Perfume ingredients that do not belong to group (a) above, but have a significantly low detection threshold, useful in the composition of the present invention, are selected from the group consisting of ambrox, bacdanol, benzyl salicylate, butyl anthranilate, cetalox, damascenone, alpha-damascone, gamma-dodecalactone, ebanol, herbavert, cis-3-hexenyl salicylate, alpha-ionone, beta-ionone, alpha-isomethylionone, lilial, methyl nonyl ketone, gamma-undecalactone, undecylenic aldehyde, and mixtures thereof. These materials are preferably present at low levels in addition to the hydrophilic ingredients of group (a), typically less than about 20%, preferably less than about 15%, more preferably less than about 10%, by weight of the total perfume compositions of the present invention. However, only low levels are required to provide an effect.

There are also hydrophilic ingredients of group (a) that have a significantly low detection threshold, and are especially useful in the composition of the present invention. Examples of these ingredients are allyl amyl glycolate, anethole, benzyl acetone, calone, cinnamic alcohol, coumarin, cyclogalbanate, Cyclal C, cymal, 4-decenal, dihydro isojasmonate, ethyl anthranilate, ethyl-2-methyl butyrate, ethyl methylphenyl glycidate, ethyl vanillin, eugenol, flor acetate, florhydral, fructone, frutene, heliotropin, keone, indole, iso cyclo citral, isoeugenol, lyral, methyl heptine carbonate, linalool, methyl anthranilate, methyl dihydrojasmonate, methyl isobutenyl tetrahydropyran, methyl beta naphthyl ketone, beta naphthol methyl ether, nerol, para-anisic aldehyde, para hydroxy phenyl butanone, phenyl acetaldehyde, vanillin, and mixtures thereof. Use of low odor detection threshold perfume ingredients minimizes the level of organic material that is released into the atmosphere.

(E). Low Molecular Weight Polyols

Low molecular weight polyols with relatively high boiling points, as compared to water, such as ethylene glycol, diethylene glycol, propylene glycol and/or glycerol are preferred optional ingredients for improving odor control performance of the composition of the present invention. Not to be bound by theory, it is believed that the incorporation of a small amount of low molecular weight glycols into the composition of the present invention enhances the formation of the cyclodextrin inclusion complexes as the fabric dries.

It is believed that the polyols' ability to remain on the fabric for a longer period of time than water, as the fabric dries allows it to form ternary complexes with the cyclodextrin and some malodorous molecules. The addition of the glycols is believed to fill up void space in the cyclodextrin cavity that is unable to be totally filled by some malodor molecules of relatively smaller sizes. Preferably the glycol used is glycerin, ethylene glycol, propylene glycol, dipropylene glycol or mixtures thereof, more preferably ethylene glycol and propylene glycol. Cyclodextrins prepared by processes that result in a level of such polyols are highly desirable, since they can be used without removal of the polyols.

Some polyols, e.g., dipropylene glycol, are also useful to facilitate the solubilization of some perfume ingredients in the composition of the present invention.

Typically, glycol is added to the composition of the present invention at a level of from about 0.01% to about 3%, by weight of the composition, preferably from about 0.05% to about 1%, more preferably from about 0.1% to about 0.5%, by weight of the composition. The preferred weight ratio of low molecular weight polyol to cyclodextrin is from about 2:1,000 to about 20:100, more preferably from about 3:1,000 to about 15:100, even more preferably from about 5:1,000 to about 10:100, and most preferably from about 1:100 to about 7:100.

(F). Optional Aminocarboxylate Chelators

Chelators, e.g., ethylenediaminetetraacetic acid (EDTA), hydroxyethylenediaminetriacetic acid, diethylenetriaminepentaacetic acid, and other aminocarboxylate chelators, and mixtures thereof, and their salts, and mixtures thereof, can optionally be used to increase antimicrobial and preservative effectiveness against Gram-negative bacteria, especially Pseudomonas species. Although sensitivity to EDTA and other aminocarboxylate chelators is mainly a characteristic of Pseudomonas species, other bacterial species highly susceptible to chelators include Achromobacter, Alcaligenes, Azotobacter, Escherichia, Salmonella, Spirillum, and Vibrio. Other groups of organisms also show increased sensitivities to these chelators, including fungi and yeasts. Furthermore, aminocarboxylate chelators can help, e.g., maintaining product clarity, protecting fragrance and perfume components, and preventing rancidity and off odors.

Although these aminocarboxylate chelators may not be potent biocides in their own right, they function as potentiators for improving the performance of other antimicrobials/preservatives in the compositions of the present invention. Aminocarboxylate chelators can potentiate the performance of many of the cationic, anionic, and nonionic antimicrobials/preservatives, phenolic compounds, and isothiazolinones, that are used as antimicrobials/preservatives in the composition of the present invention. Nonlimiting examples of cationic antimicrobials/preservatives potentiated by aminocarboxylate chelators in solutions are chlorhexidine salts (including digluconate, diacetate, and dihydrochloride salts), and Quaternium-15, also known as Dowicil 200, Dowicide Q, Preventol DI, benzalkonium chloride, cetrimonium, myristalkonium chloride, cetylpyridinium chloride, lauryl pyridinium chloride, and the like. Nonlimiting examples of useful anionic antimicrobials/preservatives which are enhanced by aminocarboxylate chelators are sorbic acid and potassium sorbate. Nonlimiting examples of useful nonionic antimicrobials/preservatives which are potentiated by aminocarboxylate chelators are DMDM hydantoin, phenethyl alcohol, monolaurin, imidazolidinyl urea, and Bronopol (2-bromo-2-nitropropane-1,3-diol).

Examples of useful phenolic antimicrobials/preservatives potentiated by these chelators are chloroxylenol, phenol, tert-butyl hydroxyanisole, salicylic acid, resorcinol, and sodium o-phenyl phenate. Nonlimiting examples of isothiazolinone antimicrobials/preservatives which are enhanced by aminocarboxylate chelators are Kathon, Proxel and Promexal.

The optional chelators are present in the compositions of this invention at levels of, typically, from about 0.01% to about 0.3%, more preferably from about 0.02% to about 0.1%, most preferably from about 0.02% to about 0.05% by weight of the usage compositions to provide antimicrobial efficacy in this invention.

Free, uncomplexed aminocarboxylate chelators are required to potentiate the efficacy of the antimicrobials. Thus, when excess alkaline earth (especially calcium and magnesium) and transitional metals (iron, manganese, copper, and others) are present, free chelators are not available and antimicrobial potentiation is not observed. In the case where significant water hardness or transitional metals are available or where product esthetics require a specified chelator level, higher levels may be required to allow for the availability of free, uncomplexed aminocarboxylate chelators to function as antimicrobial/preservative potentiators.

(G). Metal Salts

Optionally, but highly preferred, the present invention can include metallic salts for added odor absorption and/or antimicrobial benefit for the cyclodextrin solution. The metallic salts are selected from the group consisting of copper salts, zinc salts, and mixtures thereof.

Copper salts have some antimicrobial benefits. Specifically, cupric abietate acts as a fungicide, copper acetate acts as a mildew inhibitor, cupric chloride acts as a fungicide, copper lactate acts as a fungicide, and copper sulfate acts as a germicide. Copper salts also possess some malodor control abilities. See U. S. Pat. No. 3,172,817, Leupold, et al., which discloses deodorizing compositions for treating disposable articles, comprising at least slightly water-soluble salts of acylacetone, including copper salts and zinc salts, all of said patents are incorporated herein by reference.

The preferred zinc salts possess malodor control abilities. Zinc has been used most often for its ability to ameliorate malodor, e.g., in mouth wash products, as disclosed in U.S. Pat. Nos. 4,325,939, issued Apr. 20, 1982 and 4,469,674, issued Sep. 4, 1983, to N. B. Shah, et al., all of which are incorporated herein by reference. Highly-ionized and soluble zinc salts such as zinc chloride, provide the best source of zinc ions. Zinc borate functions as a fungistat and a mildew inhibitor, zinc caprylate functions as a fungicide, zinc chloride provides antiseptic and deodorant benefits, zinc ricinoleate functions as a fungicide, zinc sulfate heptahydrate functions as a fungicide and zinc undecylenate functions as a fungistat.

Preferably the metallic salts are water-soluble zinc salts, copper salts or mixtures thereof, and more preferably zinc salts, especially $ZnCl_2$. These salts are preferably present in the present invention primarily to absorb amine and sulfur-containing compounds that have molecular sizes too small to be effectively complexed with the cyclodextrin molecules. Low molecular weight sulfur-containing materials, e.g., sulfide and mercaptans, are components of many types of malodors, e.g., food odors (garlic, onion), body/perspiration odor, breath odor, etc. Low molecular weight amines are also components of many malodors, e.g., food odors, body odors, urine, etc.

When metallic salts are added to the composition of the present invention they are typically present at a level of from about 0.1% to about 10%, preferably from about 0.2% to about 8%, more preferably from about 0.3% to about 5% by weight of the usage composition. When zinc salts are used as the metallic salt, and a clear solution is desired, it is preferable that the pH of the solution is adjusted to less than about 7, more preferably less than about 6 most preferably, less than about 5, in order to keep the solution clear.

(H). Enzymes

Enzymes can be used to control certain types of malodor, especially malodor from urine and other types of excretions, including regurgitated materials. Proteases are especially desirable. The activity of commercial enzymes depends very much on the type and purity of the enzyme being considered Enzymes are normally incorporated at levels sufficient to provide up to about 5 mg by weight, preferably from about 0.001 mg to about 3 mg, more preferably from about 0.002 mg to about 1 mg, of active enzyme per gram of the aqueous compositions. Stated otherwise, the aqueous compositions herein can comprise from about 0.0001% to about 0.5%, preferably from about 0.001% to about 0.3%, more preferably from about 0.005% to about 0.2% by weight of a commercial enzyme preparation. Protease enzymes are usually present in such commercial preparations at levels sufficient to provide from 0.0005 to 0.1 Anson units (AU) of activity per gram of aqueous composition.

Nonlimiting examples of suitable, commercially available, water soluble proteases are pepsin, tripsin, ficin, bromelin, papain, rennin, and mixtures thereof. Papain can be isolated, e.g., from papaya latex, and is available commercially in the purified form of up to, e.g., about 80% protein, or cruder, technical grade of much lower activity. Other suitable examples of proteases are the subtilisins which are obtained from particular strains of *B. subtilis* and *B. licheniforms*. Another suitable protease is obtained from a strain of Bacillus, having maximum activity throughout the pH range of 8–12, developed and sold by Novo Industries A/S under the registered trade name ESPERASE®. The preparation of this enzyme and analogous enzymes is described in British Patent Specification No. 1,243,784 of Novo. Proteolytic enzymes suitable for removing protein-based stains that are commercially available include those sold under the trade names ALCALASE® and SAVINASE® by Novo Industries A/S (Denmark) and MAXATASE® by International Bio-Synthetics, Inc. (The Netherlands). Other proteases include Protease A (see European Patent Application 130,756, published Jan. 9, 1985); Protease B (see European Patent Application Ser. No. 87303761.8, filed Apr. 28, 1987, and European Patent Application 130,756, Bott et al, published Jan. 9, 1985); and proteases made by Genencor International, Inc., according to one or more of the following patents: Caldwell et al, U.S. Pat. Nos. 5,185,258, 5,204,015 and 5,244,791.

A wide range of enzyme materials and means for their incorporation into liquid compositions are also disclosed in U.S. Pat. No. 3,553,139, issued Jan. 5, 1971 to McCarty et al. Enzymes are further disclosed in U.S. Pat. No. 4.101,457, Place et al, issued Jul. 18, 1978, and in U.S. Pat. No. 4,507,219, Hughes, issued Mar. 26, 1985. Other enzyme materials useful for liquid formulations, and their incorporation into such formulations, are disclosed in U.S. Pat. No. 4,261,868, Hora et al, issued Apr. 14, 1981. Enzymes can be stabilized by various techniques, e.g., those disclosed and exemplified in U.S. Pat. No. 3,600,319, issued Aug. 17, 1971 to Gedge, et al., European Patent Application Publication No. 0 199 405, Application No. 86200586.5, published Oct. 29, 1986, Venegas, and in U.S. Pat. No. 3,519,570. All of the above patents and applications are incorporated herein, at least in pertinent part.

Enzyme-polyethylene glycol conjugates are also preferred. Such polyethylene glycol (PEG) derivatives of enzymes, wherein the PEG or alkoxy-PEG moieties are coupled to the protein molecule through, e.g., secondary amine linkages. Suitable derivatization decreases immunogenicity, thus minimizes allergic reactions, while still maintaining some enzymatic activity. An example of protease-PEG's is PEG-subtilisin Carlsberg from B. licheniformis coupled to methoxy-PEGs through secondary amine linkage, and is available from Sigma-Aldrich Corp., St. Louis, Mo.

(I). Preservative

Optionally, but preferably, solubilized, water-soluble, antimicrobial preservative can be added to the composition of the present invention if the antimicrobial material C. is not sufficient, or is not present, because cyclodextrin molecules are made up of varying numbers of glucose units which can make them a prime breeding ground for certain microorganisms, especially when in aqueous compositions. This drawback can lead to the problem of storage stability of cyclodextrin solutions for any significant length of time. Contamination by certain microorganisms with subsequent microbial growth can result in an unsightly and/or malodorous solution. Because microbial growth in cyclodextrin solutions is highly objectionable when it occurs, it is highly preferable to include a solubilized, water-soluble, antimicrobial preservative, which is effective for inhibiting and/or regulating microbial growth in order to increase storage stability of the preferably clear, aqueous odor-absorbing solution containing water-soluble cyclodextrin.

Typical microorganisms that can be found in cyclodextrin supplies and whose growth can be found in the presence of cyclodextrin in aqueous cyclodextrin solutions include bacteria, e.g., *Bacillus thuringiensis* (cereus group) and *Bacillus sphaericus;* and fungi, e.g., *Asperguillus ustus*. *Bacillus sphaericus* is one of the most numerous members of Bacillus species in soils. *Aspergillus ustus* is common in grains and flours which are raw materials to produce cyclodextrins. Microorganisms such as *Escherichia coli* and *Pseudomonas aeruginosa* are found in some water sources, and can be introduced during the preparation of cyclodextrin solutions. Other Pseudomonas species, such as *P. cepacia,* are typical microbial contaminants in surfactant manufacturing facilities and may readily contaminate packed finished products. Typical other bacterial contaminants may include Burkholderia, Enterobacter and Gluconobacter species. Representative fungal species which may be associated with agricultural soils, crops and in the case of this invention, corn products such as cyclodextrins include Asperguillus. Absidia, Penicillium, Paecilomyces, and other species.

It is preferable to use a broad spectrum preservative, e.g., one that is effective on both bacteria (both gram positive and gram negative) and fungi. A limited spectrum preservative, e.g., one that is only effective on a single group of microorganisms, e.g., fungi, can be used in combination with a broad spectrum preservative or other limited spectrum preservatives with complimentary and/or supplementary activity. A mixture of broad spectrum preservatives can also be used. In some cases where a specific group of microbial contaminants is problematic (such as Gram negatives), aminocarboxylate chelators, such as those described hereinbefore, can be used alone or as potentiators in conjunction with other preservatives. These chelators which include, e.g., ethylenediaminetetraacetic acid (EDTA), hydroxyethylenediaminetriacetic acid, diethylenetriaminepentaacetic acid, and other aminocarboxylate chelators, and mixtures thereof, and their salts, and mixtures thereof, can increase preservative effectiveness against Gram-negative bacteria, especially Pseudomonas species.

Antimicrobial preservatives useful in the present invention include biocidal compounds, i.e., substances that kill microorganisms, or biostatic compounds, i.e., substances that inhibit and/or regulate the growth of microorganisms. Preferred antimicrobial preservatives are those that are water-soluble and are effective at low levels because the organic preservatives can form inclusion complexes with the cyclodextrin molecules and compete with the malodorous molecules for the cyclodextrin cavities, thus rendering the cyclodextrins ineffective as odor controlling actives. Water-soluble preservatives useful in the present invention are those that have a solubility in water of at least about 0.3 g per 100 ml of water, i.e., greater than about 0.3% at room temperature, preferably greater than about 0.5% at room temperature. These types of preservatives have a lower affinity to the cyclodextrin cavity, at least in the aqueous phase, and are therefore more available to provide antimicrobial activity. Preservatives with a water-solubility of less than about 0.3% and a molecular structure that readily fits into the cyclodextrin cavity, have a greater tendency to form inclusion complexes with the cyclodextrin molecules, thus rendering the preservative less effective to control microbes in the cyclodextrin solution. Therefore, many well known preservatives such as short chain alkyl esters of p-hydroxybenzoic acid, commonly known as parabens; N-(4-chlorophenyl)-N'-(3,4-dichlorophenyl) urea, also known as 3,4,4'-trichlorocarbanilide or triclocarban; 2,4,4'-trichloro-2'-hydroxy diphenyl ether, commonly known as triclosan are not preferred in the present invention since they are relatively ineffective when used in conjunction with cyclodextrin.

The water-soluble antimicrobial preservative in the present invention is included at an effective amount. The term "effective amount" as herein defined means a level sufficient to prevent spoilage, or prevent growth of inadvertently added microorganisms, for a specific period of time. In other words, the preservative is not being used to kill microorganisms on the surface onto which the composition is deposited in order to eliminate odors produced by microorganisms. Instead, it is preferably being used to prevent spoilage of the cyclodextrin solution in order to increase the shelf-life of the composition. Preferred levels of preservative are from about 0.0001% to about 0.5%, more preferably from about 0.0002% to about 0.2%, most preferably from about 0.0003% to about 0.1%, by weight of the usage composition.

In order to reserve most of the cyclodextrins for odor control, the cyclodextrin to preservative molar ratio should be greater than about 5:1, preferably greater than about 10:1, more preferably greater than about 50:1, even more preferably greater than about 100:1.

The preservative can be any organic preservative material which will not cause damage to fabric appearance, e.g., discoloration, coloration, bleaching. Preferred water-soluble preservatives include organic sulfur compounds, halogenated compounds, cyclic organic nitrogen compounds, low molecular weight aldehydes, quaternary ammonium compounds, dehydroacetic acid, phenyl and phenolic compounds, and mixtures thereof.

The following are non-limiting examples of preferred water-soluble preservatives for use in the present invention. A more complete list is found in U.S. Pat. No. 5,714,137, incorporated hereinbefore by reference.

1). Organic Sulfur Compounds

Preferred water-soluble preservatives for use in the present invention are organic sulfur compounds. Some non-limiting examples of organic sulfur compounds suitable for use in the present invention are:

(a) 3-Isothiazolone Compounds

A preferred preservative is an antimicrobial, organic preservative containing 3-isothiazolone groups.

This class of compounds is disclosed in U.S. Pat. No. 4,265,899, Lewis et al., issued May 5, 1981, and incorporated herein by reference. A preferred preservative is a water-soluble mixture of 5-chloro-2-methyl-4-isothiazolin-3-one and 2-methyl-4-isothiazolin-3-one, more preferably a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Company.

When Kathon® is used as the preservative in the present invention it is present at a level of from about 0.0001% to about 0.01%, preferably from about 0.0002% to about 0.005%, more preferably from about 0.0003% to about 0.003%, most preferably from about 0.0004% to about 0.002%, by weight of the composition.

Other isothiazolins include 1,2-benzisothiazolin-3-one, available under the trade name Proxel® products; and 2-methyl-4,5-trimethylene-4-isothiazolin-3-one, available under the trade name Promexal®. Both Proxel and Promexal are available from Zeneca. They have stability over a wide pH range (i.e., 4-12). Neither contain active halogen and are not formaldehyde releasing preservatives. Both Proxel and Promexal are effective against typical Gram negative and positive bacteria, fungi and yeasts when used at a level from about 0.001% to about 0.5%, preferably from about 0.005% to about 0.05%, and most preferably from about 0.01% to about 0.02% by weight of the usage composition.

(b) Sodium Pyrithione

Another preferred organic sulfur preservative is sodium pyrithione, with water solubility of about 50%. When sodium pyrithione is used as the preservative in the present invention it is typically present at a level of from about 0.0001% to about 0.01%, preferably from about 0.0002% to about 0.005%, more preferably from about 0.0003% to about 0.003%, by weight of the usage composition.

Mixtures of the preferred organic sulfur compounds can also be used as the preservative in the present invention.

2). Halogenated Compounds

Preferred preservatives for use in the present invention are halogenated compounds. Some non-limiting examples of halogenated compounds suitable for use in the present invention are:

5-bromo-5-nitro-1,3-dioxane, available under the trade name Bronidox L® from Henkel. Bronidox L® has a solubility of about 0.46% in water. When Bronidox is used as the preservative in the present invention it is typically present at a level of from about 0.0005% to about 0.02%, preferably from about 0.001% to about 0.01%, by weight of the usage composition;

2-bromo-2-nitropropane-1,3-diol, available under the trade name Bronopol® from Inolex can be used as the preservative in the present invention. Bronopol has a solubility of about 25% in water. When Bronopol is used as the preservative in the present invention it is typically present at a level of from about 0.002% to about 0.1%, preferably from about 0.005% to about 0.05%, by weight of the usage composition;

1,1'-hexamethylene bis(5-(p-chlorophenyl)biguanide), commonly known as chlorhexidine, and its salts, e.g., with acetic and gluconic acids can be used as a preservative in the present invention. The digluconate salt is highly water-soluble, about 70% in water, and the diacetate salt has a solubility of about 1.8% in water. When chlorhexidine is used as the preservative in the present invention it is typically present at a level of from about 0.0001% to about 0.04%, preferably from about 0.0005% to about 0.01%, by weight of the usage composition.

1,1,1-Trichloro-2-methylpropan-2-ol, commonly known as chlorobutanol, with water solubility of about 0.8%; a typical effective level of chlorobutanol is from about 0.1% to about 0.5%, by weight of the usage composition.

4,4'-(Trimethylenedioxy)bis-(3-bromobenzamidine) diisethionate, or dibromopropamidine, with water solubility of about 50%; when dibromopropamidine is used as the preservative in the present invention it is typically present at a level of from about 0.0001% to about 0.05%, preferably from about 0.0005% to about 0.01% by weight of the usage composition.

Mixtures of the preferred halogenated compounds can also be used as the preservative in the present invention.

3). Cyclic Organic Nitrogen Compounds

Preferred water-soluble preservatives for use in the present invention are cyclic organic nitrogen compounds. Some non-limiting examples of cyclic organic nitrogen compounds suitable for use in the present invention are:

(a) Imidazolidinedione Compounds

Preferred preservatives for use in the present invention are imidazolidione compounds. Some non-limiting examples of imidazolidinedione compounds suitable for use in the present invention are:

1,3-bis(hydroxymethyl)-5,5-dimethyl-2,4-imidazolidinedione, commonly known as dimethyloldimethylhydantoin, or DMDM hydantoin, available as, e.g., Glydant® from Lonza. DMDM hydantoin has a water solubility of more than 50% in water, and is mainly effective on bacteria. When DMDM hydantoin is used, it is preferable that it be used in combination with a broad spectrum preservative such as Kathon CG®, or formaldehyde. A preferred mixture is about a 95:5 DMDM hydantoin to 3-butyl-2-iodopropynylcarbamate mixture, available under the trade name Glydant Plus® from Lonza. When Glydant Plus® is used as the preservative in the present invention, it is typically present at a level of from about 0.005% to about 0.2% by weight of the usage composition;

N-[1,3-bis(hydroxymethyl)2,5-dioxo-4-imidazolidinyl]-N,N'-bis(hydroxymethyl) urea, commonly known as diazolidinyl urea, available under the trade name Germall II® from Sutton Laboratories, Inc. (Sutton) can be used as the preservative in the present invention. When Germall II® is used as the preservative in the present invention, it is typically present at a level of from about 0.01% to about 0.1% by weight of the usage composition;

N,N"-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from (Sutton) can be used as the preservative in the present invention. When imidazolidinyl urea is used as the preservative, it is typically present at a level of from about 0.05% to about 0.2%, by weight of the usage composition.

Mixtures of the preferred imidazolidinedione compounds can also be used as the preservative in the present invention.

(b) Polymethoxy Bicyclic Oxazolidine

Another preferred water-soluble cyclic organic nitrogen preservative is polymethoxy bicyclic oxazolidine, available under the trade name Nuosept® C from Hüls America. When Nuosept® C is used as the preservative, it is typically present at a level of from about 0.005% to about 0.1%, by weight of the usage composition.

Mixtures of the preferred cyclic organic nitrogen compounds can also be used as the preservative in the present invention.

4). Low Molecular Weight Aldehydes (a). Formaldehyde

A preferred preservative for use in the present invention is formaldehyde. Formaldehyde is a broad spectrum preservative which is normally available as formalin which is a 37% aqueous solution of formaldehyde. When formaldehyde is used as the preservative in the present invention, typical levels are from about 0.003% to about 0.2%, preferably from about 0.008% to about 0.1%. more preferably from about 0.01% to about 0.05%, by weight of the usage composition.

(b) Glutaraldehyde

A preferred preservative for use in the present invention is glutaraldehyde. Glutaraldehyde is a water-soluble, broad spectrum preservative commonly available as a 25% or a 50% solution in water. When glutaraldehyde is used as the preservative in the present invention it is typically present at a level of from about 0.005% to about 0.1%, preferably from about 0.01% to about 0.05%, by weight of the usage composition.

5). Quaternary Compounds

Preferred preservatives for use in the present invention are cationic and/or quaternary compounds. Such compounds include polyaminopropyl biguanide, also known as polyhexamethylene biguanide having the general formula:

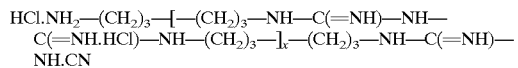

Polyaminopropyl biguanide is a water-soluble, broad spectrum preservative which is available as a 20% aqueous solution available under the trade name Cosmocil CQ® from ICI Americas, Inc., or under the trade name Mikrokill® from Brooks, Inc.

1-(3-Chlorallyl)-3,5,7-triaza-1-azoniaadamantane chloride, available, e.g., under the trade name Dowicil 200 from Dow Chemical, is an effective quaternary ammonium preservative; it is freely soluble in water; however, it has the tendency to discolor (yellow), therefore it is not highly preferred.

Mixtures of the preferred quaternary ammonium compounds can also be used as the preservative in the present invention.

When quaternary ammonium compounds are used as the preservative in the present invention, they are typically present at a level of from about 0.005% to about 0.2%, preferably from about 0.01% to about 0.1%, by weight of the usage composition.

6). Dehydroacetic Acid

A preferred preservative for use in the present invention is dehydroacetic acid. Dehydroacetic acid is a broad spectrum preservative preferably in the form of a sodium or a potassium salt so that it is water-soluble. This preservative acts more as a biostatic preservative than a biocidal preservative. When dehydroacetic acid is used as the preservative it is typically used at a level of from about 0.005% to about 0.2%, preferably from about 0.008% to about 0.1%, more preferably from about 0.01% to about 0.05%, by weight of the usage composition.

7). Phenyl and Phenolic Compounds

Some non-limiting examples of phenyl and phenolic compounds suitable for use in the present invention are:

4,4'-diamidino-α,ω-diphenoxypropane diisethionate, commonly known as propamidine isethionate, with water solubility of about 16%; and 4,4'-diamidino-α,ω-diphenoxyhexane diisethionate, commonly known as hexamidine isethionate. Typical effective level of these salts is about 0.0002% to about 0.05% by weight of the usage composition.

Other examples are benzyl alcohol, with a water solubility of about 4%; 2-phenylethanol, with a water solubility of about 2%; and 2-phenoxyethanol, with a water solubility of about 2.67%; typical effective level of these phenyl and phenoxy alcohol is from about 0.1% to about 0.5%, by weight of the usage composition.

8). Mixtures thereof

The preservatives of the present invention can be used in mixtures in order to control a broad range of microorganisms.

Bacteriostatic effects can sometimes be obtained for aqueous compositions by adjusting the composition pH to an acid pH, e.g., less than about pH 4, preferably less than about pH 3, or a basic pH, e.g., greater than about 10, preferably greater than about 11. Low pH for microbial control is not a preferred approach in the present invention because the low pH can cause chemical degradation of the cyclodextrins. High pH for microbial control is also not preferred because at high pH's, e.g., greater than about 10, preferably greater than about 11, the cyclodextrins can be ionized and their ability to complex with organic materials is reduced. Therefore, aqueous compositions of the present invention should have a pH of from about 3 to about 10, preferably from about 4 to about 8, more preferably from about 4.5 to about 6. The pH is typically adjusted with inorganic molecules to minimize complexation with cyclodextrin.

(J). Cyclodextrin Compatible Wrinkle Control Agent

The composition can also optionally contain an effective amount of a cyclodextrin-compatible fabric wrinkle control agent, preferably selected from the group consisting of: fiber lubricant, shape retention polymer, hydrophilic plasticizer, lithium salt, and mixtures thereof.

1) Cyclodextrin Compatible Fiber Lubricants

The present invention can use a cyclodextrin compatible fiber lubricant to impart a lubricating property or increased gliding ability to fibers in fabric, particularly clothing. Not to be bound by theory, it is believed that water and other alcoholic solvents break or weaken the hydrogen bonds that hold the wrinkles, the cyclodextrin compatible fabric lubricant facilitates the fibers to glide on one another to further release the fibers from the wrinkle condition in wet or damp fabric. After the fabric is dried, the residual silicone can provide lubricity to reduce the tendency of fabric rewrinkling.

a) Cyclodextrin Compatible Silicone

The present invention can use silicone to impart a lubricating property or increased gliding ability to fibers in fabric, particularly clothing. The silicone useful in providing fiber lubricity in the composition of the present invention should be cyclodextrin-compatible, that is it should not substantially form complex with cyclodextrin so as to diminish performance of the cyclodextrin and/or the silicone. Complex formation diminishes both the ability of the cyclodextrin to absorb odors and the ability of the silicone to provide fiber lubricity. The preferred cyclodextrin compatible silicones have pendant alkyl groups having less than about 8, preferably less than about 6, carbon atoms, and do not have pendant aryl groups. Nonlimiting examples of useful silicones include noncurable silicones such as polydimethylsilicone and volatile silicones, and curable silicones such as aminosilicones and hydroxysilicones. When the composition of this invention is to be dispensed from a spray dispenser in a consumer household setting, the noncurable silicones such as polydimethylsilicone, especially the volatile silicones, are preferred. Curable and/or reactive silicones such as amino-functional silicones silicones and silicones with reactive groups such as Si—OH, Si—H, silanes, and the like, are not preferred in this situation, because the portion of the composition that is sprayed but misses the garment, and falls instead on flooring surfaces, such as rugs, carpets, concrete floors, tiled floors, linoleum floors, bathtub floors, can leave a silicone layer that is accumulated and/or cured and/or bonded to the flooring surfaces. Such silicones that are accumulated on such surfaces, and especially those that are bonded to such surfaces are difficult to remove. Flooring surfaces thus become slippery and can present a safety hazard to the household members. The curable and reactive silicones can be used in compositions specifically designed for use in enclosed areas such as in a dewrinkling cabinet. Many types of aminofunctional silicones also cause fabric yellowing. Thus, the silicones that cause fabric discoloration are also not preferred.

The word "silicone" as used herein preferably refers to emulsified and/or microemulsified silicones, including those that are commercially available and those that are emulsified and/or microemulsified in the composition, unless otherwise described. Some non-limiting examples of silicones which are useful in the present invention are: non-volatile silicone fluids such as polydimethyl siloxane gums and fluids; volatile silicone fluid which can be a cyclic silicone fluid of the formula $[(CH_3)_2SiO]_n$ where n ranges between about 3 to about 7, preferably about 5, or a linear silicone polymer fluid having the formula $(CH_3)_3SiO[(CH_3)_2SiO]_mSi(CH_3)_3$ where m can be 0 or greater and has an average value such that the viscosity at 25° C. of the silicone fluid is preferably about 5 centistokes or less.

Thus one type of silicone that is useful in the composition of the present invention is polyalkyl silicone with the following structure:

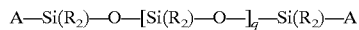

The alkyl groups substituted on the siloxane chain (R) or at the ends of the siloxane chains (A) can have any structure as long as the resulting silicones remain fluid at room temperature and do not substantially form a complex with cyclodextrin.

Each R group preferably is alkyl, hydroxy, or hydroxyalkyl group, and mixtures thereof, having less than about 8, preferably less than about 6 carbon atoms, more preferably, each R group is methyl, ethyl, propyl, hydroxy group, and mixtures thereof, most preferably each R group is methyl. Aryl, alkylaryl and/or arylalkyl groups are not preferred. Each A group which blocks the ends of the silicone chain is hydrogen, methyl, methoxy, ethoxy, hydroxy, propoxy, and mixtures thereof, preferably methyl. q is preferably an integer from about 7 to about 8,000. The preferred silicones are polydimethyl siloxanes; more preferred silicones are polydimethyl siloxanes having a viscosity of from about 10 to about 1,000,000 centistokes at 25° C. Mixtures of volatile silicones and non-volatile polydimethyl siloxanes are also preferred. Suitable examples include silicones offered by Dow Corning Corporation and General Electric Company. Preferably, the silicones are hydrophobic; are neither irritating, toxic, nor otherwise harmful when applied to fabric or when they come in contact with human skin; are compatible with other components of the composition beside cyclodextrin; are chemically stable under normal use and storage conditions; and are capable of being deposited on fabric.

Suitable methods for preparing these silicone materials are disclosed in U.S. Pat. Nos. 2,826,551 and 3,964,500, incorporated herein by reference. Silicones useful in the present invention are also commercially available. Suitable examples include silicones offered by Dow Corning Corporation and General Electric Company.

Other useful silicone materials, but less preferred than polydimethyl polysiloxane, include materials of the formula:

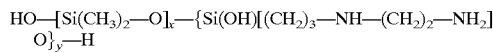

wherein x and y are integers which depend on the molecular weight of the silicone, preferably having a viscosity of from about 10,000 cst to about 500,000 cst at 25° C. This material is also known as "amodimethicone". Although silicones with a high number, e.g., greater than about 0.5 millimolar equivalent of amine groups can be used, they are not preferred because they can cause fabric yellowing.

Similarly, silicone materials which can be used correspond to the formulas:

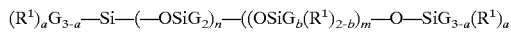

wherein G is selected from the group consisting of hydrogen, OH, and/or $C_1$–$C_5$ alkyl; a denotes 0 or an integer from 1 to 3; b denotes 0 or 1; the sum of n+m is a number from 1 to about 2,000; $R^1$ is a monovalent radical of formula $C_pH_{2p}L$ in which p is an integer from 2 to 4 and L is selected from the group consisting of:

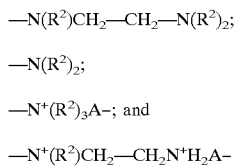

wherein each $R^2$ is chosen from the group consisting of hydrogen, a $C_1$–$C_5$ saturated hydrocarbon radical, and each $A^-$ denotes compatible anion, e.g., a halide ion; and

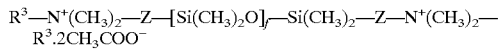

wherein

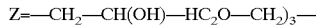

$R^3$ denotes a long chain alkyl group; and f denotes an integer of at least about 2.

In the formulas herein, each definition is applied individually and averages are included.

Another silicone material which can be used, but is less preferred than polydimethyl siloxanes, has the formula:

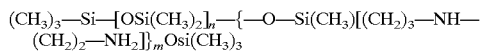

wherein n and m are the same as before. The preferred silicones of this type are those which do not cause fabric discoloration.

Alternatively, the silicone material can be provided as a moiety or a part of a non-silicone molecule. Examples of such materials are copolymers containing silicone moieties, typically present as block and/or graft copolymers.

When silicone is present, it is present at least an effective amount to provide lubrication of the fibers, typically from about 0.1% to about 5%, preferably from about 0.2% to about 3%, more preferably from about 0.3% to about 2%, by weight of the usage composition.

b) Synthetic Solid Particles

Solid polymeric particles of average particle size smaller than about 10 microns, preferably smaller than 5 microns, more preferably smaller than about 1 micron, e.g., Velustrol P-40 oxidized polyethylene emulsion available from Clariant, can be used as a lubricant, since they can provide a "roller-bearing" action. When solid polymeric particles are present, they are present at an effective amount to provide lubrication of the fibers, typically from about 0.01% to about 3%, preferably from about 0.05% to about 1%, more preferably from about 0.1% to about 0.5%, by weight of the usage composition.

2) Cyclodextrin Compatible Shape Retention Polymer

These polymers can be natural, or synthetic, and can act by forming a film, and/or by providing adhesive properties. E.g., the present invention can optionally use film-forming and/or adhesive polymer to impart shape retention to fabric, particularly clothing. By "adhesive" it is meant that when applied as a solution or a dispersion to a fiber surface and dried, the polymer can attach to the surface. The polymer can form a film on the surface, or when residing between two fibers and in contact with the two fibers, it can bond the two fibers together. Other polymers such as starches can form a film and/or bond the fibers together when the treated fabric is pressed by a hot iron. Such a film will have adhesive strength, cohesive breaking strength, and cohesive breaking strain.

The polymer useful in providing shape retention in the composition of the present invention should be cyclodextrin-compatible, that is it should not substantially form complex with cyclodextrin so as to diminish performance of the cyclodextrin and/or the polmer. Complex formation affects both the ability of the cyclodextrin to absorb odors and the ability of the polymer to impart shape retention to fabric.

Nonlimiting examples for natural polymers are starches and their derivatives, and chitins and their derivatives.

The synthetic polymers useful in the present invention are comprised of monomers. Some nonlimiting examples of monomers which can be used to form the synthetic polymers of the present invention include: low molecular weight $C_1$–$C_6$ unsaturated organic mono- and polycarboxylic acids, such as acrylic acid, methacrylic acid, crotonic acid, maleic acid and its half esters, itaconic acid, and mixtures thereof; esters of said acids with $C_1$–$C_6$ alcohols, such as methanol, ethanol. 1-propanol, 2-propanol, 1-butanol, 2-methyl-1-propanol, 1-pentanol, 2-pentanol, 3-pentanol. 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, and the like, and mixtures thereof. Nonlimiting examples of said esters are methyl acrylate, ethyl acrylate, t-butyl acrylate, methyl methacrylate, hydroxyethyl methacrylate, methoxy ethyl methacrylate, and mixtures thereof; amides and imides of said acids, such as N,N-dimethylacrylamide, N-t-butyl acrylamide, maleimides; low molecular weight unsaturated alcohols such as vinyl alcohol (produced by the hydrolysis of vinyl acetate after polymerization), allyl alcohol; esters of said alcohols with low molecular weight carboxylic acids, such as, vinyl acetate, vinyl propionate; ethers of said alcohols such as methyl vinyl ether; polar vinyl heterocyclics, such as vinyl pyrrolidone, vinyl caprolactam, vinyl pyridine, vinyl imidazole, and mixtures thereof; other unsaturated amines and amides, such as vinyl amine, diethylene triamine, dimethylaminoethyl methacrylate, ethenyl formamide; vinyl sulfonate; salts of acids and amines listed above; low molecular weight unsaturated hydrocarbons and derivatives such as ethylene, propylene, butadiene, cyclohexadiene, vinyl chloride; vinylidene chloride; and mixtures thereof and alkyl quaternized derivatives thereof, and mixtures thereof. Preferably, said monomers are selected from the group consisting of vinyl alcohol; acrylic acid; methacrylic acid; methyl acrylate; ethyl acrylate; methyl methacrylate; t-butyl acrylate; t-butyl methacrylate; n-butyl acrylate; n-butyl methacrylate; dimethylaminoethyl methacrylate; N,N-dimethyl acrylamide; N,N-dimethyl methacrylamide; N-t-butyl acrylamide; vinylpyrrolidone; vinyl pyridine; adipic acid; diethylenetriamine; salts thereof and alkyl quaternized derivatives thereof, and mixtures thereof. Monomers which provide pendant groups that can complex with cyclodextrin are not preferred because they can form complex with cyclodextrin. Examples of such monomers are acrylic or methacrylic acid esters of $C_7$–$C_{18}$ alcohols, such as neodecanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, and 1-decanol; styrene; t-butylstyrene; vinyl toluene; and the like.

Preferably, said monomers form homopolymers and/or copolymers (i.e., the film-forming and/or adhesive polymer) having a glass transition temperature (Tg) of from about −20° C. to about 150° C., preferably from about −10° C. to about 150° C., more preferably from about 0° C. to about 100° C., most preferably, the adhesive polymer hereof, when dried to form a film will have a Tg of at least about 25° C., so that they are not unduly sticky, or "tacky" to the touch. Preferably said polymer is soluble and/or dispersible in water and/or alcohol. Said polymer typically has a molecular weight of at least about 500, preferably from about 1,000 to about 2,000,000, more preferably from about 5,000 to about 1,000,000, and even more preferably from about 30,000 to about 300,000 for some polymers.

Some non-limiting examples of homopolymers and copolymers which can be used as film-forming and/or adhesive polymers of the present invention are: adipic acid/dimethylaminohydroxypropyl diethylenetriamine copolymer; adipic acid/epoxypropyl diethylenetriamine copolymer; poly(vinylpyrrolidone/dimethylaminoethyl methacrylate); polyvinyl alcohol; polyvinylpyridine n-oxide; methacryloyl ethyl betaine/methacrylates copolymer; ethyl acrylate/methyl methacrylate/methacrylic acid/ acrylic acid copolymer; polyamine resins; and polyquaternary amine resins; poly(ethenylformamide); poly (vinylamine) hydrochloride; poly(vinyl alcohol-co-6% vinylamine); poly(vinyl alcohol-co-12% vinylamine); poly (vinyl alcohol-co-6% vinylamine hydrochloride); and poly (vinyl alcohol-co-12% vinylamine hydrochloride). Preferably, said copolymer and/or homopolymers are selected from the group consisting of adipic acid/ dimethylaminohydroxypropyl diethylenetriamine copolymer; poly(vinylpyrrolidone/dimethylaminoethyl methacrylate); polyvinyl alcohol; ethyl acrylate/methyl methacrylate/methacrylic acid/acrylic acid copolymer; methacryloyl ethyl betaine/methacrylates copolymer; polyquaternary amine resins; poly(ethenylformamide); poly (vinylamine) hydrochloride; poly(vinyl alcohol-co-6% vinylamine); poly(vinyl alcohol-co-12% vinylamine); poly (vinyl alcohol-co-6% vinylamine hydrochloride); and poly (vinyl alcohol-co-12% vinylamine hydrochloride).

Nonlimiting examples of the preferred polymer that are commercially available are: polyvinylpyrrolidone/ dimethylaminoethyl methacrylate copolymer, such as Copolymer 958®, molecular weight of about 100,000 and Copolymer 937, molecular weight of about 1,000,000, available from GAF Chemicals Corporation; adipic acid/ dimethylaminohydroxypropyl diethylenetriamine copolymer, such as Cartaretin F-4®, and F-23, available from Sandoz Chemicals Corporation; methacryloyl ethyl betaine/methacrylates copolymer, such as Diaformer Z-SM®, available from Mitsubishi Chemicals Corporation; polyvinyl alcohol copolymer resin, such as Vinex 2019®, available from Air Products and Chemicals or Moweol®, available from Clariant; adipic acid/epoxypropyl diethylenetriamine copolymer, such as Delsette 101®, available from Hercules Incorporated; polyamine resins, such as Cypro 515®, available from Cytec Industries; polyquaternary amine resins, such as Kymene 557H®, available from Hercules Incorporated; and polyvinylpyrrolidone/acrylic acid, such as Sokalan EG 310®, available from BASF.

Preferred polymers useful in the present invention are selected from the group consisting of copolymers of hydrophilic monomers and hydrophobic monomers. The polymer can be linear random or block copolymers, and mixtures thereof. Such hydrophobic/hydrophilic copolymers typically have a hydrophobic monomer/hydrophilic monomer ratio of from about 95:5 to about 20:80, preferably from about 90:10 to about 40:60, more preferably from about 80:20 to about 50:50 by weight of the copolymer. The hydrophobic monomer can comprise a single hydrophobic monomer or a mixture of hydrophobic monomers, and the hydrophilic monomer can comprise a single hydrophilic monomer or a mixture of hydrophilic monomers. The term "hydrophobic" is used herein consistent with its standard meaning of lacking affinity for water, whereas "hydrophilic" is used herein consistent with its standard meaning of having affinity for water. As used herein in relation to monomer units and polymeric materials, including the copolymers, "hydrophobic" means substantially water insoluble; "hydrophilic" means substantially water soluble. In this regard, "substantially water insoluble" shall refer to a material that is not soluble in distilled (or equivalent) water, at 25° C., at a concentration of about 0.2% by weight, and preferably not soluble at about 0.1% by weight (calculated on a water plus monomer or polymer weight basis). "Substantially water soluble" shall refer to a material that is soluble in distilled (or equivalent) water, at 25° C., at a concentration of about 0.2% by weight, and are preferably soluble at about 1% by weight. The terms "soluble", "solubility" and the like, for purposes hereof, corresponds to the maximum concentration of monomer or polymer, as applicable, that can dissolve in water or other solvents to form a homogeneous solution, as is well understood to those skilled in the art.

Nonlimiting examples of useful hydrophobic monomers are acrylic acid $C_1$–$C_6$ alkyl esters, such as methyl acrylate, ethyl acrylate, t-butyl acrylate; methacrylic $C_1$–$C_6$ alkyl esters, such as methyl methacrylate, methoxy ethyl methacrylate; vinyl alcohol esters of carboxylic acids, such as, vinyl acetate, vinyl propionate, vinyl ethers, such as methyl vinyl ether; vinyl chloride; vinylidene chloride; ethylene, propylene and other unsaturated hydrocarbons; and the like; and mixtures thereof. Some preferred hydrophobic monomers are methyl acrylate, methyl methacrylate, t-butyl acrylate, t-butyl methacrylate, n-butyl acrylate, n-butyl methacrylate, and mixtures thereof.

Nonlimiting examples of useful hydrophilic monomers are unsaturated organic mono- and polycarboxylic acids, such as acrylic acid, methacrylic acid, crotonic acid, maleic acid and its half esters, itaconic acid; unsaturated alcohols, such as vinyl alcohol, allyl alcohol; polar vinyl heterocyclics, such as vinyl pyrrolidone, vinyl caprolactam, vinyl pyridine, vinyl imidazole; vinyl amine; vinyl sulfonate; unsaturated amides, such as acrylamides, e.g., N,N-dimethylacrylamide, N-t-butyl acrylamide; hydroxyethyl methacrylate; dimethylaminoethyl methacrylate; salts of acids and amines listed above; and the like; and mixtures thereof. Some preferred hydrophilic monomers are acrylic acid, methacrylic acid, N,N-dimethyl acrylamide, N,N-dimethyl methacrylamide, N-t-butyl acrylamide, dimethylamino ethyl methacrylate, vinyl pyrrolidone, salts thereof and alkyl quaternized derivatives thereof, and mixtures thereof.

Non limiting examples of polymers for use in the present invention include the following, where the composition of the copolymer is given as approximate weight percentage of each monomer used in the polymerization reaction used to prepare the polymer: vinyl pyrrolidone/vinyl acetate copolymers (at ratios of up to about 30% by weight of vinyl pyrrolidone); vinyl pyrrolidone/vinyl acetate/butyl acrylate copolymer (10/78/12 and 10/70/20); vinyl pyrrolidone/vinyl propionate copolymer (5/95); vinyl caprolactam/vinyl acetate copolymer (5/95); and resins sold under the trade names Ultrahold CA 8® by Ciba Geigy (ethyl acrylate/acrylic acid/N-t-butyl acrylamide copolymer); Resyn 28–1310® by National Starch and Luviset CA 66® y BASF (vinyl acetate/crotonic acid copolymer 90/10); Luviset CAP® by BASF (vinyl acetate/vinyl propionate/crotonic acid 50/40/10); Amerhold DR-25® by Union Carbide (ethyl acrylate/methacrylic acid/methyl methacrylate/acrylic acid copolymer), and Poligen A® by BASF (polyacrylate dispersion). One highly preferred polymer is composed of acrylic acid and t-butyl acrylate monomeric units, preferably with acrylic acid/t-butyl acrylate ratio of from about 90:10 to about 10:90, preferably from about 70:30 to about 15:85, more preferably from about 50:50 to about 20:80, by weight of the polymer. Nonlimiting examples of acrylic acid/tert-butyl acrylate copolymers useful in the present invention are those with an approximate acrylic acid/tert-butyl acrylate weight ratio of about 25:75 and an average molecular weight of from about 70,000 to about 100,000, and those with an approximate acrylic acid/tert-butyl acrylate weight ratio of about 35:65 and an average molecular weight of from about 60,000 to about 90,000.

The film-forming and/or adhesive polymer of the present invention is present at least an effective amount to provide shape retention, typically from about 0.05% to about 5%, preferably from about 0.1% to about 3%, more preferably from about 0.2% to about 2%, even more preferably from about 0.3% to about 1%, by weight of the usage composition.

The adhesive polymer is present in the composition in a sufficient amount to result in an amount of from about 0.001% to about 1%, preferably from about 0.01% to about 0.5%, more preferably from about 0.02% to about 0.4% by weight of polymer per weight of dry fabrics.

It is not intended to exclude the use of higher or lower levels of the polymers, as long as an effective amount is used to provide adhesive and film-forming properties to the composition and the composition can be formulated and effectively applied for its intended purpose.

Concentrated compositions can also be used in order to provide a less expensive product. When a concentrated product is used, i.e., when the wrinkle reducing active is from about 5% to about 50%, by weight of the concentrated composition, it is preferable to dilute the composition before treating fabric. Preferably, the wrinkle reducing active is diluted with about 50% to about 10,000%, more preferably from about 50% to about 8,000%, and even more preferably from about 50% to about 5,000%, by weight of the composition, of water.

Silicones and film-forming polymers can be combined to produce preferred wrinkle reducing actives. Typically the weight ratio of silicone to film-forming polymer is from about 10:1 to about 1:10, preferably from about 5: 1 to about 1:5, and more preferably from about 2:1 to about 1:2. Typically, the preferred wrinkle reducing active of silicone plus polymer is present at a level of from about 0.1% to about 8%, preferably from about 0.3% to about 5%, more preferably from about 0.5% to about 3%, by weight of the composition.

Other preferred adhesive and/or film forming polymers that are useful in the composition of the present invention actually contain silicone moieties in the polymers themselves, typically present as block and/or graft copolymers.

The preferred polymers for use herein have the characteristic of providing a natural appearing "drape" in which the fabric does not form wrinkles, or resist deformation.

Starch

Starch is not normally preferred, since it makes the fabric resistant to deformation. However, it does provide increased "body" which is often desired. Starch is particularly preferred in compositions of this invention to be used with ironing. When used, starch is solubilized or dispersed in the composition. Any type of starch, e.g. those derived from corn, wheat, rice, grain sorghum, waxy grain sorghum, waxy maize or tapioca, or mixtures thereof and water soluble or dispersible modifications or derivatives thereof, can be used in the composition of the present invention. Modified starches that can be used include natural starches that have been degraded to obtain a lower viscosity by acidic, oxidative or enzymic depolymerization. Additionally, low viscosity commercially available propoxylated and/or ethoxylated starches are useable in the present composition and are preferred since their low viscosity at relatively high solids concentrations make them very adaptable to spraying processes. Suitable alkoxylated, low viscosity starches are submicron sized particles of hydrophobic starch that are readily dispersed in water and are prepared by alkoxylation of granular starch with a monofunctional alkoxylating agent which provides the starch with ether linked hydrophilic groups. A suitable method for their preparation is taught in U.S. Pat. No. 3,462,283. In accordance with the invention, the propoxylated or ethoxylated starch derivatives are dispersed in the aqueous medium in an amount of from about 0.1% to about 10%, preferably from about 0.5% to about 6%, more preferably from about 1% to about 4% by weight of the usage composition.

Preferred pH Range

Compositions according to the present invention, which contain a shape retention polymer having hydrophilic monomers with an acid functional pending group, such as acrylic acid, methacrylic acid, crotonic acid, maleic acid and its half esters, itaconic acid, and mixtures thereof, preferably are adjusted to have a pH of greater than about 6.5, preferably from about 7 and about 11, more preferably from about 8 to about 10.5, most preferably from about 9 to about 10.5 to improve the solubility of the polymer. Above pH 11, the ability of cyclodextrin to form complexes and to control odor is diminished. This is achieved by the addition of a caustic alkali. Example of suitable caustic alkalis for use herein include sodium and potassium hydroxide.

These polymers, by themselves, also provide odor control to some amine type malodors. If amine malodor control is desired, the pH of the solution should be kept as low as possible, preferably from about 4 to about 8, more preferably from about 6.5 to about 7.5.

3) Optional Cyclodextrin-Compatible Hydrophilic Plasticizer

Optionally, the composition can contain a cyclodextrin-compatible hydrophilic plasticizer to soften both the fabric fibers, especially cotton fibers, and the adhesive and/or film-forming shape retention polymers. Examples of the preferred hydrophilic plasticizers are short chain polyhydric alcohols, such as is glycerol, ethylene glycol, propylene glycol, diethylene glycol, dipropylene glycol, sorbitol, erythritol or mixtures thereof, more preferably diethylene glycol, dipropylene glycol, ethylene glycol, propylene glycol and mixtures thereof.

The aqueous compositions containing these plasticizers also tend to provide a slower drying profile for clothing/fabrics, to allow time for any wrinkles to disappear when the clothing/fabrics are hung to dry. This is balanced by the desire by most consumer to have the garments to dry faster. Therefore, when needed, the plasticizers should be used at an effective, but as low as possible, level in the composition. When a hydrophilic plasticizer is used, it is present in the at a level of from 0.01% to 5%, preferably from 0.05% to 2%, more preferably from 0.1% to 1% by weight of the usage composition.

(4) Lithium Salts

Lithium salts are disclosed to be used as solubilizing aids in the production silk fibroin using lithium bromide, e.g., U.S. Pat. No. 4,233,212, issued Nov. 11, 1980 to Otoi et al., and lithium thiocyanate, e.g., U.S. Pat. No. 5,252,285, issued Oct. 12, 1993 to Robert L. Lock. U.S. Pat. No. 5,296,269, issued Mar. 22, 1994 to Yang et al. discloses a process to produce crease-resistant silk using lithium bromide and lithium chloride. U.S. Pat. No. 5,199,954, issued Apr. 6, 1993 to Schultz et al. discloses a hair dye composition containing lithium bromide. Lithium salts are disclosed as static control agents in a liquid softener composition in U.S. Pat. No. 4,069,159, issued Jan. 17, 1978 to Mason Hayek. All of these patents are incorporated herein by reference.

It is now found that aqueous composition comprising lithium salts and lithium salt hydrates provides improved fabric wrinkle control. Lithium salts that are useful in the present invention are cyclodextrin compatible lithium salts. Cyclodextrin compatible lithium salts are those having counterions that do not have the tendency to form a complex with cyclodextrin. Nonlimiting examples of cyclodextrin compatible lithium salts that are useful in the present invention are lithium bromide, lithium bromide hydrate, lithium chloride, lithium chloride hydrate, lithium acetate, lithium acetate dihydrate, lithium lactate, lithium sulfate, lithium sulfate monohydrate, lithium tartrate, lithium bitartrate, and mixtures thereof, preferably lithium bromide, lithium lactate, and mixtures thereof. Some water soluble salts such as lithium benzoate are not preferred because they can form complex with cyclodextrin. Useful levels of lithium salts are from about 0.1% to about 10%, preferably from about 0.5% to about 7%, more preferably from about 1% to about 5%, by weight of the usage composition.

(5) Mixtures Thereof

As stated hereinbefore, the composition can also contain mixtures of fiber lubricant, shape retention polymer, plasticizer, and/or lithium salts.

(K) Carrier

Aqueous solutions are preferred for odor control. The dilute aqueous solution provides the maximum separation of cyclodextrin molecules on the fabric and thereby maximizes the chance that an odor molecule will interact with a cyclodextrin molecule.

The preferred carrier of the present invention is water. The water which is used can be distilled, deionized, or tap water. Water is the main liquid carrier due to its low cost, availability, safety, and environmental compatibility. Water not only serves as the liquid carrier for the cyclodextrins, but it also facilitates the complexation reaction between the cyclodextrin molecules and any malodorous molecules that are on the fabric when it is treated. It has recently been discovered that water has an unexpected odor controlling effect of its own. It has been discovered that the intensity of the odor generated by some polar, low molecular weight organic amines, acids, and mercaptans is reduced when the odor-contaminated fabrics are treated with an aqueous solution. Not to be bound by theory, it is believed that water solubilizes and depresses the vapor pressure of these polar, low molecular weight organic molecules, thus reducing their odor intensity.

Water is also very useful for fabric wrinkle removal or reduction. Not to be bound by theory, it is believed that water breaks many intrafiber and interfiber hydrogen bonds that keep the fabric in a wrinkle state. It also swells, lubricates and relaxes the fibers to help the wrinkle removal process.

The level of liquid carrier in the compositions of the present invention is typically greater than about 80%, preferably greater than about 90%, more preferably greater than about 95%, by weight of the composition. When a concentrated composition is used, the level of liquid carrier is typically from about 50% to about 98%, by weight of the composition, preferably from about 60% to about 97%, more preferably from about 70% to about 95%, by weight of the composition.

Optionally, in addition to water, the carrier can contain a low molecular weight organic solvent that is highly soluble in water, e.g., ethanol, propanol, isopropanol, and the like, and mixtures thereof. Low molecular weight alcohols can help the treated fabric to dry faster. The optional solvent is also useful in the solubilization of some shape retention polymers described hereinbefore. The optional water soluble low molecular weight solvent can be used at a level of up to about 50%, typically from about 1% to about 20%, preferably from about 2% to about 15%, more preferably from about 5% to about 10%, by weight of the total composition. Factors that need to consider when a high level of solvent is used in the composition are odor, flammability, and environment impact.

(L) Other Optional Ingredients

The composition of the present invention can optionally contain adjunct odor-controlling materials, chelating agents, antistatic agents, insect and moth repelling agents, colorants, especially bluing agents, antioxidants, and mixtures thereof in addition to the cyclodextrin molecules. The total level of optional ingredients is low, preferably less than about 5%, more preferably less than about 3%, and even more preferably less than about 2%, by weight of the usage composition. These optional ingredients exclude the other ingredients specifically mentioned hereinbefore. Incorporating adjunct odor-controlling materials can enhance the capacity of the cyclodextrin to control odors as well as broaden the range of odor types and molecule sizes which can be controlled. Such materials include, for example, metallic salts, water-soluble cationic and anionic polymers, zeolites, water-soluble bicarbonate salts, and mixtures thereof.

(1). Water-Soluble Polyionic Polymers

Some water-soluble polyionic polymers, e.g., water-soluble cationic polymer and water-soluble anionic polymers can be used in the composition of the present invention to provide additional odor control benefits.

a. Cationic Polymers, e.g., Polyamines

Water-soluble cationic polymers, e.g., those containing amino functionalities, amido functionalities, and mixtures thereof, are useful in the present invention to control certain acid-type odors.

b. Anionic Polymers, e.g., Polyacrylic Acid

Water-soluble anionic polymers, e.g., polyacrylic acids and their water-soluble salts are useful in the present invention to control certain amine-type odors. Preferred polyacrylic acids and their alkali metal salts have an average molecular weight of less than about 20,000, preferably less than 10,000, more preferably from about 500 to about 5,000. Polymers containing sulfonic acid groups, phosphoric acid groups, phosphonic acid groups, and their water-soluble salts, and mixtures thereof, and mixtures with carboxylic acid and carboxylate groups, are also suitable.

Water-soluble polymers containing both cationic and anionic functionalities are also suitable. Examples of these polymers are given in U.S. Pat. No. 4,909,986, issued Mar. 20, 1990 to N. Kobayashi and A. Kawazoe, incorporated herein by reference. Another example of water-soluble polymers containing both cationic and anionic functionalities is a copolymer of dimethyldiallyl ammonium chloride and acrylic acid, commercially available under the trade name Merquat 280® from Calgon.

When a water-soluble polymer is used it is typically present at a level of from about 0.001% to about 3%, preferably from about 0.005% to about 2%, more preferably from about 0.01% to about 1%, and even more preferably from about 0.05% to about 0.5%, by weight of the usage composition.

(2). Soluble Carbonate and/or Bicarbonate Salts

Water-soluble alkali metal carbonate and/or bicarbonate salts, such as sodium bicarbonate, potassium bicarbonate, potassium carbonate, cesium carbonate, sodium carbonate, and mixtures thereof can be added to the composition of the present invention in order to help to control certain acid-type odors. Preferred salts are sodium carbonate monohydrate, potassium carbonate, sodium bicarbonate, potassium bicarbonate, and mixtures thereof. When these salts are added to the composition of the present invention, they are typically present at a level of from about 0.1% to about 5%, preferably from about 0.2% to about 3%, more preferably from about 0.3% to about 2%, by weight of the composition. When these salts are added to the composition of the present invention it is preferably that incompatible metal salts not be present in the invention. Preferably, when these salts are used the composition should be essentially free of zinc and other incompatible metal ions, e.g., Ca, Fe, Ba, etc. which form water-insoluble salts.

(3). Additional Odor Absorbers

When the clarity of the solution is not needed, and the solution is not sprayed on fabrics, other optional odor absorbing materials, e.g., zeolites and/or activated carbon, can also be used.

(a). Zeolites

A preferred class of zeolites is characterized as "intermediate" silicate/aluminate zeolites. The intermediate zeolites are characterized by $SiO_2/AlO_2$ molar ratios of less than about 10. Preferably the molar ratio of $SiO_2/AlO_2$ ranges from about 2 to about 10. The intermediate zeolites have an advantage over the "high" zeolites. The intermediate zeolites have a higher affinity for amine-type odors, they are more weight efficient for odor absorption because they have a larger surface area, and they are more moisture tolerant and retain more of their odor absorbing capacity in water than the high zeolites. A wide variety of intermediate zeolites suitable for use herein are commercially available as Valfor® CP301-68, Valfort® 300-63, Valfor® CP300-35, and Valfor® CP300-56, available from PQ Corporation, and the CBV100® series of zeolites from Conteka.

Zeolite materials marketed under the trade name Abscents® and Smellrite®, available from The Union Carbide Corporation and UOP are also preferred. These materials are typically available as a white powder in the 3–5 micron particle size range. Such materials are preferred over the intermediate zeolites for control of sulfur-containing odors, e.g., thiols, mercaptans.

(b). Activated Carbon

The carbon material suitable for use in the present invention is the material well known in commercial practice as an absorbent for organic molecules and/or for air purification purposes. Often, such carbon material is referred to as "activated" carbon or "activated" charcoal. Such carbon is available from commercial sources under such trade names as; Calgon-Type CPG®; Type PCB®; Type SGL®; Type CAL®; and Type OL®.

(4). Antistatic Agents

The composition of the present invention can optionally contain an effective amount of antistatic agent to provide the treated clothes with in-wear static. Preferred antistatic agents are those that are water soluble in at least an effective amount, such that the composition remains a clear solution. Examples of these antistatic agents are monoalkyl cationic quaternary ammonium compounds, e.g., mono($C_{10}$–$C_{14}$ alkyl)trimethyl ammonium halide, such as monolauryl trimethyl ammonium chloride, hydroxycetyl hydroxyethyl dimethyl ammonium chloride, available under the trade name Dehyquart E® from Henkel, and ethyl bis(polyethoxy ethanol) alkylammonium ethylsulfate, available under the trade name Variquat 66® from Witco Corp., polymeric quaternary ammonium salts, such as polymers conforming to the general formula:

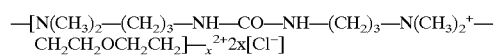

available under the trade name Mirapol A-15® from Rhône-Poulenc, and

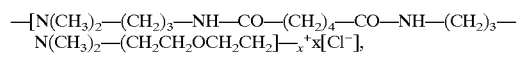

available under the trade name Mirapol AD-1® from Rhône-Poulenc, quaternized polyethyleneimines, vinylpyrrolidone/methacrylamidopropyltrimethylammonium chloride copolymer, available under the trade name Gafquat HS-100® from GAF; triethonium hydrolyzed collagen ethosulfate, available under the trade name Quat-Pro E® from Maybrook; neutralized sulfonated polystyrene, available, e.g., under the trade name Versa TL-130® from Alco Chemical, neutralized sulfonated styrene/maleic anhydride copolymers, available, e.g., under the trade name Versa TL-4® from Alco Chemical; polyethylene glycols; and mixtures thereof.

It is preferred that a no foaming, or low foaming, agent is used, to avoid foam formation during fabric treatment. It is also preferred that polyethoxylated agents such as polyethylene glycol or Variquat 66® are not used when alpha-cyclodextrin is used. The polyethoxylate groups have a strong affinity to, and readily complex with, alpha-cyclodextrin which in turn depletes the uncomplexed cyclodextrin available for odor control.

When an antistatic agent is used it is typically present at a level of from about 0.05% to about 10%, preferably from about 0.1% to about 5%, more preferably from about 0.3% to about 3%, by weight of the usage composition.

(6). Insect and/or Moth Repelling Agent

The composition of the present invention can optionally contain an effective amount of insect and/or moth repelling agents. Typical insect and moth repelling agents are pheromones, such as anti-aggregation pheromones, and other natural and/or synthetic ingredients. Preferred insect and moth repellent agents useful in the composition of the present invention are perfume ingredients, such as citronellol, citronellal, citral, linalool, cedar extract, geranium oil, sandalwood oil, 2-(diethylphenoxy)ethanol, 1-dodecene, etc. Other examples of insect and/or moth repellents useful in the composition of the present invention are disclosed in U.S. Pat. Nos. 4,449,987, 4,693,890, 4,696, 676, 4,933,371, 5,030,660, 5,196,200, and in "Semio Activity of Flavor and Fragrance Molecules on Various Insect Species", B. D. Mookherjee et al., published in *Bioactive Volatile Compounds from Plants,* ASC Symposium Series 525, R. Teranishi, R. G. Buttery, and H. Sugisawa, 1993, pp. 35–48, all of said patents and publications being incorporated herein by reference. When an insect and/or moth repellent is used it is typically present at a level of from about 0.005% to about 3%, by weight of the usage composition.

(6). Colorant

Colorants and dyes, especially bluing agents, can be optionally added to the odor absorbing compositions for visual appeal and performance impression. When colorants are used, they are used at extremely low levels to avoid fabric staining. Preferred colorants for use in the present compositions are highly water-soluble dyes, e.g., Liquitint® dyes available from Milliken Chemical Co. Non-limiting examples of suitable dyes are, Liquitint Blue HP®, Liquitint Blue 65®, Liquitint Patent Blue®, Liquitint Royal Blue®, Liquitint Experimental Yellow 8949-43®, Liquitint Green HMC®, Liquitint Yellow II®, and mixtures thereof, preferably Liquitint Blue HP®, Liquitint Blue 65®, Liquitint Patent Blue®, Liquitint Royal Blue®, Liquitint Experimental Yellow 8949-43®, and mixtures thereof.

(8). Optional Anti-Clogging Agent

Optional anti-clogging agent which enhances the wetting and anti-clogging properties of the composition, especially when starch is present, is chosen from the group of polymeric glycols of alkanes and olefins having from 2 to about 6, preferably 2 carbon atoms. The anti-clogging agent inhibits the formation of "plugs" in the spray nozzle. An example of the preferred anti-clogging agent is polyethylene glycol having an average molecular weight of from about 800 to about 12,000, more preferably from about 1,400 to about 8,000. When used, the anti-clogging agent is present at a level of from about 0.01% to about 1%, preferably from about 0.05% to about 0.5%, more preferably, from about 0.1% to about 0.3% by weight of the usage composition.

(9). Mixtures Thereof

II. Article of Manufacture

The composition of the present invention can also be used in an article of manufacture comprising said composition plus a spray dispenser. When the commercial embodiment of the article of manufacture is used, it is optional, but preferable, to include the preservative. Therefore, the most basic article of manufacture comprises uncomplexed cyclodextrin, a carrier, and a spray dispenser.

Spray Dispenser

The article of manufacture herein comprises a spray dispenser. The cyclodextrin composition is placed into a spray dispenser in order to be distributed onto the fabric. Said spray dispenser for producing a spray of liquid droplets can be any of the manually activated means as is known in the art, e.g. trigger-type, pump-type, non-aerosol self-pressurized, and aerosol-type spray means, for treating the odor-absorbing composition to small fabric surface areas and/or small articles, as well as non-manually operated, powered sprayers for conveniently treating the odor-absorbing composition to large fabric surface areas and/or a large number of garments and/or articles. The spray dispenser herein does not normally include those that will substantially foam the clear, aqueous odor absorbing composition. It has been found that the performance is increased by providing smaller particle droplets. Desirably, the Sauter mean particle diameter is from about 10 $\mu$m to about 120 $\mu$m, more preferably, from about 20 $\mu$m to about 100 $\mu$m. Dewrinkling benefits are improved by providing small particles (droplets), as discussed hereinbefore, especially when the surfactant is present.

The spray dispenser can be an aerosol dispenser. Said aerosol dispenser comprises a container which can be constructed of any of the conventional materials employed in fabricating aerosol containers. The dispenser must be capable of withstanding internal pressure in the range of from about 20 to about 110 p.s.i.g., more preferably from about 20 to about 70 p.s.i.g. The one important requirement concerning the dispenser is that it be provided with a valve member which will permit the clear, aqueous odor absorbing composition contained in the dispenser to be dispensed in the form of a spray of very fine, or finely divided, particles or droplets. The aerosol dispenser utilizes a pressurized sealed container from which the clear, aqueous odor-absorbing composition is dispensed through a special actuator/valve assembly under pressure. The aerosol dispenser is pressurized by incorporating therein a gaseous component generally known as a propellant. Common aerosol propellants, e.g., gaseous hydrocarbons such as isobutane, and mixed halogenated hydrocarbons, which are not preferred. Halogenated hydrocarbon propellants such as chlorofluoro hydrocarbons have been alleged to contribute to environmental problems. Hydrocarbon propellants can form complexes with the cyclodextrin molecules thereby reducing the availability of uncomplexed cyclodextrin molecules for odor absorption. Preferred propellants are compressed air, nitrogen, inert gases, carbon dioxide, etc. A more complete description of commercially available aerosol-spray dispensers appears in U.S. Pat. Nos.: 3,436,772, Stebbins, issued Apr.8, 1969; and 3,600,325, Kaufman et al., issued Aug. 17, 1971; both of said references are incorporated herein by reference.

Preferably the spray dispenser can be a self-pressurized non-aerosol container having a convoluted liner and an elastomeric sleeve. Said self-pressurized dispenser comprises a liner/sleeve assembly containing a thin, flexible radially expandable convoluted plastic liner of from about 0.010 to about 0.020 inch thick, inside an essentially cylindrical elastomeric sleeve. The liner/sleeve is capable of holding a substantial quantity of odor-absorbing fluid product and of causing said product to be dispensed. A more complete description of self-pressurized spray dispensers can be found in U.S. Pat. Nos. 5,111,971, Winer, issued May 12, 1992, and 5,232,126, Winer, issued Aug. 3, 1993; both of said references are herein incorporated by reference. Another type of aerosol spray dispenser is one wherein a barrier separates the odor absorbing composition from the propellant (preferably compressed air or nitrogen), as disclosed in U.S. Pat. No. 4,260,110, issued Apr. 7, 1981, and incorporated herein by reference. Such a dispenser is available from EP Spray Systems, East Hanover, N.J.

More preferably, the spray dispenser is a non-aerosol, manually activated, pump-spray dispenser. Said pump-spray dispenser comprises a container and a pump mechanism which securely screws or snaps onto the container. The container comprises a vessel for containing the aqueous odor-absorbing composition to be dispensed.

The pump mechanism comprises a pump chamber of substantially fixed volume, having an opening at the inner end thereof. Within the pump chamber is located a pump stem having a piston on the end thereof disposed for reciprocal motion in the pump chamber. The pump stem has a passageway there through with a dispensing outlet at the outer end of the passageway and an axial inlet port located inwardly thereof.

The container and the pump mechanism can be constructed of any conventional material employed in fabricating pump-spray dispensers, including, but not limited to: polyethylene; polypropylene; polyethyleneterephthalate; blends of polyethylene, vinyl acetate, and rubber elastomer. A preferred container is made of clear, e.g., polyethylene terephthalate. Other materials can include stainless steel. A more complete disclosure of commercially available dispensing devices appears in: U.S. Pat. Nos.: 4,895,279, Schultz, issued Jan. 23, 1990; 4,735,347, Schultz et al., issued Apr. 5, 1988; and 4,274,560, Carter, issued Jun. 23, 1981; all of said references are herein incorporated by reference.

Most preferably, the spray dispenser is a manually activated trigger-spray dispenser. Said trigger-spray dispenser comprises a container and a trigger both of which can be constructed of any of the conventional material employed in fabricating trigger-spray dispensers, including, but not limited to: polyethylene; polypropylene; polyacetal; polycarbonate; polyethyleneterephthalate; polyvinyl chloride; polystyrene; blends of polyethylene, vinyl acetate, and rubber elastomer. Other materials can include stainless steel and glass. A preferred container is made of clear, e.g. polyethylene terephthalate. The trigger-spray dispenser does not incorporate a propellant gas into the odor-absorbing composition, and preferably it does not include those that will foam the odor-absorbing composition. The trigger-spray dispenser herein is typically one which acts upon a discrete amount of the odor-absorbing composition itself, typically by means of a piston or a collapsing bellows that displaces the composition through a nozzle to create a spray of thin liquid. Said trigger-spray dispenser typically comprises a pump chamber having either a piston or bellows which is movable through a limited stroke response to the trigger for varying the volume of said pump chamber. This pump chamber or bellows chamber collects and holds the product for dispensing. The trigger spray dispenser typically has an outlet check valve for blocking communication and flow of fluid through the nozzle and is responsive to the pressure inside the chamber. For the piston type trigger sprayers, as the trigger is compressed, it acts on the fluid in the chamber and the spring, increasing the pressure on the fluid. For the bellows spray dispenser, as the bellows is compressed, the pressure increases on the fluid. The increase in fluid pressure in either trigger spray dispenser acts to open the top outlet check valve. The top valve allows the product to be forced through the swirl chamber and out the nozzle to form a discharge pattern. An adjustable nozzle cap can be used to vary the pattern of the fluid dispensed.

For the piston spray dispenser, as the trigger is released, the spring acts on the piston to return it to its original position. For the bellows spray dispenser, the bellows acts as the spring to return to its original position. This action causes a vacuum in the chamber. The responding fluid acts to close the outlet valve while opening the inlet valve drawing product up to the chamber from the reservoir.

A more complete disclosure of commercially available dispensing devices appears in U.S. Pat. Nos. 4,082,223, Nozawa, issued Apr. 4, 1978; 4,161,288, McKinney, issued Jul. 17, 1985; 4,434,917, Saito et al., issued Mar. 6, 1984; and 4,819,835, Tasaki, issued Apr. 11, 1989; 5,303,867, Peterson, issued Apr. 19, 1994; all of said references are incorporated herein by reference.

A broad array of trigger sprayers or finger pump sprayers are suitable for use with the compositions of this invention. These are readily available from suppliers such as Calmar, Inc., City of Industry, California; CSI (Continental Sprayers, Inc.), St. Peters, Mo.; Berry Plastics Corp., Evansville, Ind., a distributor of Guala® sprayers; or Seaquest Dispensing, Cary, Ill.

The preferred trigger sprayers are the blue inserted Guala® sprayer, available from Berry Plastics Corp., or the Calmar TS800-1A®, TS1300®, and TS-800-2®, available from Calmar Inc., because of the fine uniform spray characteristics, spray volume, and pattern size. More preferred are sprayers with precompression features and finer spray characteristics and even distribution, such as Yoshino sprayers from Japan. Any suitable bottle or container can be used with the trigger sprayer, the preferred bottle is a 17 fl-oz. bottle (about 500 ml) of good ergonomics similar in shape to the Cinch® bottle. It can be made of any materials such as high density polyethylene, polypropylene, polyvinyl chloride, polystyrene, polyethylene terephthalate, glass, or any other material that forms bottles. Preferably, it is made of high density polyethylene or clear polyethylene terephthalate.

For smaller fluid ounce sizes (such as 1 to 8 ounces), a finger pump can be used with canister or cylindrical bottle. The preferred pump for this application is the cylindrical Euromist II® from Seaquest Dispensing. More preferred are those with precompression features.

The article of manufacture herein can also comprise a non-manually operated spray dispenser (sprayer). By "non-manually operated" it is meant that the spray dispenser can be manually activated, but the force required to dispense the odor absorbing composition is provided by another, non-manual means. Non-manually operated sprayers include, but are not limited to, powered sprayers, air aspirated sprayers, liquid aspirated sprayers, electrostatic sprayers, and nebulizer sprayers. The odor absorbing composition is placed into a spray dispenser in order to be distributed onto the fabric.

Powered sprayers include self contained powered pumps that pressurize the aqueous odor absorbing composition and dispense it through a nozzle to produce a spray of liquid droplets. Powered sprayers are attached directly or remotely through the use of piping/tubing to a reservoir (such as a bottle) to hold the aqueous odor absorbing composition. Powered sprayers may include, but are not limited to, centrifugal or positive displacement designs. It is preferred that the powered sprayer be powered by a portable DC electrical current from either disposable batteries (such as commercially available alkaline batteries) or rechargeable battery units (such as commercially available nickel cadmium battery units). Powered sprayers may also be powered by standard AC power supply available in most buildings. The discharge nozzle design can be varied to create specific spray characteristics (such as spray diameter and particle size). It is also possible to have multiple spray nozzles for different spray characteristics. The nozzle may or may not contain an adjustable nozzle shroud that would allow the spray characteristics to be altered.

Nonlimiting examples of commercially available powered sprayers are disclosed in U.S. Pat. Nos. 4,865,255, Luvisotto, issued Sep. 12, 1989 which is incorporated herein by reference. Preferred powered sprayers are readily available from suppliers such as Solo, Newport News, Va. (e.g., Solo Spraystar™ rechargeable sprayer, listed as manual part #: US 460 395) and Multi-sprayer Systems, Minneapolis, Minnesota (e.g., model: Spray 1).

Air aspirated sprayers include the classification of sprayers generically known as "air brushes". A stream of pressurized air draws up the aqueous odor absorbing composition and dispenses it through a nozzle to create a spray of liquid. The odor absorbing composition can be supplied via separate piping/tubing or more commonly is contained in ajar to which the aspirating sprayer is attached.

Nonlimiting examples of commercially available air aspirated sprayers appears in U.S. Pat. Nos. 1,536,352, Murray, issued Apr. 22, 1924 and 4,221,339, Yoshikawa, issues Sep. 9, 1980; all of said references are incorporated herein by reference. Air aspirated sprayers are readily available from suppliers such as The Badger Air-Brush Co, Franklin Park, Ill. (e.g., model #: 155) and Wilton Air Brush Equipment, Woodridge, Ill. (e.g., stock #: 415–4000, 415–4001, 415–4100).

Liquid aspirated sprayers are typical of the variety in widespread use to spray garden chemicals. The aqueous odor absorbing composition is drawn into a fluid stream by means of suction created by a Venturi effect. The high turbulence serves to mix the aqueous odor absorbing composition with the fluid stream (typically water) in order to provide a uniform mixture/concentration. It is possible with this method of delivery to dispense the aqueous concentrated odor absorbing composition of the present invention and then dilute it to a selected concentration with the delivery stream.

Liquid aspirated sprayers are readily available from suppliers such as Chapin Manufacturing Works, Batavia, N.Y. (e.g., model #: 6006).

Electrostatic sprayers impart energy to the aqueous odor absorbing composition via a high electrical potential. This energy serves to atomize and charge the aqueous odor absorbing composition, creating a spray of fine, charged particles. As the charged particles are carried away from the sprayer, their common charge causes them to repel one another. This has two effects before the spray reaches the target. First, it expands the total spray mist. This is especially important when spraying to fairly distant, large areas. The second effect is maintenance of original particle size. Because the particles repel one another, they resist collecting together into large, heavier particles like uncharged particles do. This lessens gravity's influence, and increases the charged particle reaching the target. As the mass of negatively charged particles approach the target, they push electrons inside the target inwardly, leaving all the exposed surfaces of the target with a temporary positive charge. The resulting attraction between the particles and the target overrides the influences of gravity and inertia. As each particle deposits on the target, that spot on the target becomes neutralized and no longer attractive. Therefore, the next free particle is attracted to the spot immediately adjacent and the sequence continues until the entire surface of the target is covered. Hence, charged particles improve distribution and reduce drippage.

Nonlimiting examples of commercially available electrostatic sprayers appears in U.S. Pat. Nos. 5,222,664, Noakes, issued Jun. 29, 1993; 4,962,885, Coffee, issued Oct. 16, 1990; 2,695,002, Miller, issued November 1954; 5,405,090, Greene, issued Apr. 11, 1995; 4,752,034, Kuhn, issued Jun. 21, 1988; 2,989,241, Badger, issued June 1961; all of said patents are incorporated herein by reference. Electrostatic sprayers are readily available from suppliers such as Tae In Tech Co, South Korea and Spectrum, Houston, Tex.

Nebulizer sprayers impart energy to the aqueous odor absorbing composition via ultrasonic energy supplied via a transducer. This energy results in the aqueous odor absorbing composition to be atomized. Various types of nebulizers include, but are not limited to, heated, ultrasonic, gas, venturi, and refillable nebulizers.

Nonlimiting examples of commercially available nebulizer sprayers appears in U.S. Pat. Nos. 3,901,443, Mitsui, issued Aug. 26, 1975; 2,847,248, Schmitt, issued Aug. 1958; 5,511,726, Greenspan, issued Apr. 30, 1996; all of said patents are incorporated herein by reference. Nebulizer sprayers are readily available from suppliers such as A&D Engineering, Inc., Milpitas, Calif. (e.g., model A&D Un-231 ultrasonic handy nebulizer) and Amici, Inc., Spring City, Pa. (model: swirler nebulizer).

The preferred article of manufacture herein comprises a non-manually operated sprayer, such as a battery-powered sprayer, containing the aqueous odor absorbing composition. More preferably the article of manufacture comprises a combination of a non-manually operated sprayer and a separate container of the aqueous odor absorbing composition, to be added to the sprayer before use and/or to be separated for filling/refilling. The separate container can contain an usage composition, or a concentrated composition to be diluted before use, and/or to be used with a diluting sprayer, such as with a liquid aspirated sprayer, as described herein above. Also, as described hereinbefore, the separate container should have structure that mates with the rest of the sprayer to ensure a solid fit without leakage, even after motion, impact, etc. and when handled by inexperienced consumers.

III. Method of Use

The cyclodextrin solution, which contains, e.g., surfactant, antimicrobial compound, and/or wrinkle control agent, etc., can be used by distributing, e.g., by placing, an effective amount of the aqueous solution onto the surface or article to be treated. Distribution can be achieved by using a spray device, a roller, a pad, etc., preferably a spray dispenser. For odor control, an effective amount, as defined herein, means an amount sufficient to absorb odor to effect a noticeable reduction in the perceived odor, preferably to the point that it is not discernible, by the human sense of smell. Preferably, the amount of solution is not so much as to saturate or create a pool of liquid on said article or surface and so that when dry there is no visual deposit readily discernible. For wrinkle control, an effective amount means an amount sufficient to remove or noticeably reduce the appearance of wrinkles on fabric.

Preferably, the present invention does not encompass distributing the cyclodextrin solution on to shiny surfaces including, e.g., chrome, glass, smooth vinyl, leather, shiny plastic, shiny wood, etc. It is preferable not to distribute the cyclodextrin solution onto shiny surfaces because spotting and filming can more readily occur on such surfaces. However, when appearance is not important, the composition of the present invention can be sprayed onto shiny surfaces to obtain odor control benefit. Although the cyclodextrin solution can be used on human skin, care should be taken, especially when an antimicrobial active is present in the composition.

The compositions and articles of the present invention which contain a fabric wrinkle control agent can be used to treat fabrics, garments, and the like to remove or reduce, undesirable wrinkles, in addition to the removal or reduction of undesirable odor on said objects.

An effective amount of the liquid composition of the present invention is preferably sprayed onto fabrics, particularly clothing. When the composition is sprayed onto fabric, an effective amount should be deposited onto the fabric, with the fabric becoming damp or totally saturated with the composition, typically from about 5% to about 150%, preferably from about 10% to about 100%, more preferably from about 20% to about 75%, by weight of the fabric. The amount of active typically sprayed onto the fabric is from about 0.002% to about 5%, preferably from about 0.01% to about 1%, more preferably from about 0.03% to about 0.5%, by weight of the fabric. It is highly preferable to use the preferred particles sizes described hereinbefore, since the areas that receive too much liquid will be slow to dry. Once an effective amount of the composition is sprayed onto the fabric the fabric is optionally, but preferably stretched. The fabric is typically stretched perpendicular to the wrinkle. The fabric can also be smoothed by hand after it has been sprayed. The smoothing movement works particularly well on areas of clothing that have an interface sewn into them, or on the hems of clothing. Once the fabric has been sprayed and optionally, but preferably, stretched, it is hung until dry.

The compositions of the present invention can also be used as ironing aids, especially when the fabric wrinkle control agent is a fiber lubricant. An effective amount of the composition can be sprayed onto fabric and the fabric is ironed at the normal temperature at which it should be ironed. The fabric can either be sprayed with an effective amount of the composition, allowed to dry and then ironed, or sprayed and ironed immediately.

In a still further aspect of the invention, the composition can be sprayed onto fabrics by in an in-home de-wrinkling chamber containing the fabric to be deodorized and/or dewrinkled, thereby providing ease of operation. Conventional personal as well as industrial deodorizing and/or de-wrinkling apparatuses are suitable for use herein. Traditionally, these apparatuses act by a steaming process which effects a relaxation of the fibers. Examples of home dewrinkling chambers include shower stalls. The spraying of the composition or compounds onto the fabrics can then occur within the chamber of the apparatus or before placing the fabrics into the chamber. Again, the spraying means should preferably be capable of providing droplets with a weight average diameter of from about 8 to about 100 μm, preferably from about 10 to about 50 μm. Preferably, the loading of moisture on fabrics made of natural and synthetic fibers is from about 5 to about 25%, more preferably from about 5 to about 10% by weight of the dried fabric. Other conventional steps that can be carried out in the dewrinkling apparatus can be applied such as heating and drying. Preferably, for optimum dewrinkling benefit, the temperature profile inside the chamber ranges from about 40° C. to about 80° C., more preferably from about 50° C. to about 70° C. The preferred length of the drying cycle is from about 15 to about 60 minutes, more preferably from about 20 to about 45 minutes.

The steaming step in the dewrinkling apparatus may also be eliminated if the composition is maintained at a temperature range from about 22° C. (about 72° F.) to about 76° C. (170° F.) before spraying.

The present invention also encompasses the method of spraying an effective amount of cyclodextrin solution onto household surfaces. Preferably said household surfaces are selected from the group consisting of countertops, cabinets, walls, floors, bathroom surfaces and kitchen surfaces so long as the composition does not cause an unacceptable appearance or a safety hazard. However, the anti wrinkling benefit is primarily seen on, e.g., curtains etc.

The present invention encompasses the method of spraying a mist of an effective amount of cyclodextrin solution onto fabric and/or fabric articles. Preferably, said fabric and/or fabric articles include, but are not limited to, clothes, curtains, drapes, upholstered furniture, carpeting, bed linens, bath linens, tablecloths, sleeping bags, tents, car interiors, etc.

The compositions herein are especially useful, when used to treat garments for extending the time before another wash cycle is needed. Such garments include uniforms and other garments which are normally treated in an industrial process, which can be refreshed and the time between treatments extended.

The present invention also encompasses the methods of spraying a mist of an effective amount of cyclodextrin solution onto and into shoes wherein said shoes are not sprayed to saturation; shower curtains; garbage cans and/or recycling bins. The present invention also relates to the method of spraying a mist of an effective amount of cyclodextrin solution into the air to absorb malodor. The present invention relates to the method of spraying a mist of an effective amount of cyclodextrin solution into and/or onto major household appliances including, but not limited to: refrigerators, freezers, washing machines, automatic dryers, ovens, microwave ovens, dishwashers, cat litter, pet bedding and pet houses to absorb malodor. However, it is recognized that all of these methods make use of the cyclodextrin and not the anti-wrinkling agent.

The present invention relates to the method of spraying a mist of an effective amount of cyclodextrin solution onto household pets to absorb malodor. Depending on the pet, this may also provide an anti-wrinkling benefit.

The presence of the highly preferred surfactant promotes spreading of the solution and the highly preferred antimicrobial active provides improved odor control as well as antimicrobial action, by minimizing the formation of odors. Both the surfactant and the antimicrobial active provide improved performance and the mixture is especially good. When the compositions are applied in the form of the very small particles (droplets), as disclosed hereinbefore, additional benefits are found, since the distribution is even further improved and overall performance is improved.

All percentages, ratios, and parts herein, in the Specification, Examples, and claims are by weight and are the normal approximations unless otherwise stated.

The following are non-limiting examples of the instant composition. Perfume compositions that are used herein are as follows:

| Perfume<br>Perfume Ingredients | A<br>Wt. % | B<br>Wt. % | C<br>Wt. % |
| --- | --- | --- | --- |
| Anisic aldehyde | — | — | 2 |
| Benzophenone | 3 | 5 | — |
| Benzyl acetate | 10 | 15 | 5 |
| Benzyl salicylate | 5 | 20 | 5 |
| Cedrol | 2 | — | — |
| Citronellol | 10 | — | 5 |
| Coumarin | — | — | 5 |
| Cymal | — | — | 3 |
| Dihydromyrcenol | 10 | — | 5 |
| Flor acetate | 5 | — | 5 |
| Galaxolide | 10 | — | — |
| Lilial | 10 | 15 | 20 |
| Linalyl acetate | 4 | — | 5 |
| Linalool | 6 | 15 | 5 |
| Methyl dihydro jasmonate | 3 | 10 | 5 |
| Phenyl ethyl acetate | 2 | 5 | 1 |
| Phenyl ethyl acetate | 15 | 10 | 20 |
| alpha-Terpineol | 5 | — | 8 |

-continued

| | | | |
|---|---|---|---|
| Vanillin | — | — | 1 |
| Total | 100 | 100 | 100 |

| Perfume<br>Perfume Material | D<br>Wt. % | E<br>Wt. % |
|---|---|---|
| Amyl salicylate | 8 | — |
| Benzyl acetate | 8 | 8 |
| Benzyl Salicylate | — | 2 |
| Citronellol | 7 | 27 |
| Dihydromyrcenol | 2 | — |
| Eugenol | 4 | — |
| Flor acetate | 8 | — |
| Galaxolide | 1 | — |
| Geraniol | 5 | — |
| Hexyl cinnamic aldehyde | 2 | — |
| Hydroxycitronellal | 3 | — |
| Lilial | 2 | — |
| Linalool | 12 | 13 |
| Linalyl acetate | 5 | — |
| Lyral | 3 | — |
| Methyl dihydrojasmonate | 3 | — |
| Nerol | 2 | — |
| Phenoxy ethyl propionate | — | 3 |
| Phenylethyl acetate | 5 | 17 |
| Phenylethyl alcohol | 8 | 17 |
| alpha-Terpineol | 5 | 13 |
| alpha-Terpinene | 5 | — |
| Tetrahydromyrcenol | 2 | — |
| Total | 100 | 100 |

| Perfume F<br>Perfume Ingredients | Wt. % |
|---|---|
| Benzophenone | 0.50 |
| Benzyl acetate | 3.00 |
| Benzyl propionate | 1.00 |
| beta gamma Hexenol | 0.20 |
| Cetalox | 0.10 |
| cis 3 Hexenyl acetate | 0.15 |
| cis Jasmone | 0.10 |
| cis-3-Hexenyl salicylate | 1.00 |
| Citral | 0.50 |
| Citronellal nitrile | 0.70 |
| Citronellol | 3.65 |
| Coumarin | 0.70 |
| Cyclal C | 0.30 |
| Cyclo galbanate | 0.40 |
| beta Damascone | 0.05 |
| Dihydro myrcenol | 1.00 |
| Ebanol | 0.50 |
| Flor acetate | 5.00 |
| Florhydral | 0.70 |
| Fructone | 8.50 |
| Frutene | 3.00 |
| Geranyl nitrile | 0.40 |
| Heliotropin | 0.70 |
| Hydroxycitronellal | 2.50 |
| Linalool | 2.00 |
| Linalyl acetate | 1.50 |
| Methyl dihydro jasmonate | 5.00 |
| Methyl heptine carbonate | 0.05 |
| Methyl iso butenyl tetrahydro pyran | 0.15 |
| Methyl phenyl carbinyl acetate | 0.50 |
| Nonalactone | 1.50 |
| P. T. Bucinal | 8.40 |
| para Hydroxy phenyl butanone | 1.30 |
| Phenoxy ethanol | 28.55 |
| Phenyl ethyl acetate | 0.80 |
| Phenyl ethyl alcohol | 10.00 |
| Prenyl acetate | 1.50 |
| Terpineol | 1.50 |
| Verdox | 2.10 |
| Vanillin | 0.50 |
| Total | 100.00 |

-continued

| Perfume G<br>Perfume Ingredients | Wt. % |
|---|---|
| Anisic aldehyde | 2.80 |
| Benzyl acetone | 1.00 |
| cis 3 Hexenyl acetate | 0.30 |
| Citronellal nitrile | 1.30 |
| Citronellol | 6.90 |
| Coumarin | 1.30 |
| Cyclal C | 0.30 |
| Cyclo galbanate | 0.70 |
| Cymal | 1.05 |
| delta Damascone | 0.05 |
| Dihydro myrcenol | 1.30 |
| Dipropylene glycol | 10.20 |
| Dodecalactone | 0.50 |
| Ebanol | 0.10 |
| Ethyl vanillin | 0.10 |
| Flor acetate | 8.00 |
| Florhydral | 1.30 |
| Fructone | 6.00 |
| Galaxolide (50% in isopropyl myristate) | 4.00 |
| gamma Methyl ionone | 1.00 |
| Geranyl nitrile | 0.30 |
| Helional | 1.50 |
| Hydroxycitronellal | 2.00 |
| Iso bornyl acetate | 1.80 |
| Ligustral | 0.10 |
| Linalool | 2.50 |
| Methyl dihydro jasmonate | 6.20 |
| Methyl heptine carbonate | 0.10 |
| Methyl iso butenyl tetrahydro pyran | 0.30 |
| Methyl phenyl carbinyl acetate | 1.00 |
| Orange terpenes | 2.00 |
| P. T. Bucinal | 10.00 |
| Phenyl ethyl alcohol | 20.00 |
| Prenyl acetate | 1.50 |
| Verdox | 2.50 |
| Total | 100.00 |

EXAMPLES I

| Examples<br>Ingredients | Ia<br>Wt % | Ib<br>Wt % | Ic<br>Wt % | Id<br>Wt % | Ie<br>Wt % | If<br>Wt % |
|---|---|---|---|---|---|---|
| HPBCD[a] | 1.0 | — | 1.0 | — | 1.0 | — |
| RAMEB[b] | — | 1.0 | — | 1.0 | — | 0.8 |
| D5 volatile silicone | 0.5 | 0.5 | 0.5 | 0.35 | 1.0 | — |
| PDMS 10,000 cst | — | — | — | 0.35 | — | 0.5 |
| Silwet L-7600 | 0.5 | — | — | — | 0.1 | — |
| Silwet L-7602 | — | 0.5 | — | 0.7 | — | 0.5 |
| Silwet L-7622 | — | — | 0.5 | — | 1.0 | — |
| Propylene glycol | 0.06 | — | — | — | 0.1 | — |
| Kathon | 3 ppm | 3 ppm | 3 ppm | 3 ppm | 3 ppm | 3 ppm |
| Distilled water | Bal. | Bal. | Bal. | Bal. | Bal. | Bal. |

[a]Hydroxypropyl-beta-cyclodextrin.
[b]Randomly methylated-beta-cyclodextrin.

EXAMPLES II

| Examples<br>Ingredients | IIa<br>Wt % | IIb<br>Wt % | IIc<br>Wt % | IId<br>Wt % | IIe<br>Wt % | IIf<br>Wt % |
|---|---|---|---|---|---|---|
| HPBCD | 1.0 | — | 1.0 | — | 1.0 | — |
| RAMEB | — | 1.9 | — | 1.0 | — | 0.8 |
| Lithium bromide | 3.0 | — | 2.0 | 3.0 | — | 3.0 |
| Lithium lactate | — | 3.0 | — | — | 2.5 | — |

-continued

| Examples Ingredients | IIa Wt % | IIb Wt % | IIc Wt % | IId Wt % | IIe Wt % | IIf Wt % |
|---|---|---|---|---|---|---|
| D5 volatile silicone | 0.5 | — | — | 0.35 | 1.0 | — |
| PDMS 10,000 cst | — | — | — | 0.35 | — | 0.5 |
| Silwet L-7600 | 0.5 | — | — | — | 0.1 | — |
| Silwet L-7604 | — | 0.1 | — | 0.7 | — | 0.5 |
| Silwet L-7622 | — | — | — | — | 1.0 | — |
| Propylene glycol | 0.06 | — | — | — | 0.1 | — |
| Kathon | 3 ppm | 3 ppm | 3 ppm | 3 ppm | 3 ppm | 3 ppm |
| Distilled water | Bal. | Bal. | Bal. | Bal. | Bal. | Bal. |

EXAMPLES III

| Examples Ingredients | IIIa Wt % | IIIb Wt % | IIIc Wt % | IIId Wt % | IIIe Wt % | IIIf Wt % |
|---|---|---|---|---|---|---|
| HPBCD | 1.0 | — | 1.0 | — | 1.0 | — |
| RAMEB | — | 1.0 | — | 1.0 | — | 0.8 |
| Zn Cl$_2$ | 1.0 | 1.0 | 0.7 | 1.0 | 0.7 | 0.7 |
| LiBr | 3.0 | 2.0 | 3.0 | 3.0 | — | 3.0 |
| LiSO$_4$ | — | — | — | — | 2.0 | — |
| D5 volatile silicone | 0.5 | 0.5 | — | 0.35 | 1.0 | — |
| PDMS 10,000 cst | — | — | — | 0.35 | — | 0.5 |
| Silwet L-7600 | 0.5 | — | — | — | 0.1 | — |
| Silwet L-7602 | — | 0.5 | — | 0.7 | — | 0.5 |
| Silwet L-7622 | — | — | — | — | 1.0 | — |
| Perfume A | 0.1 | — | — | — | — | — |
| Perfume B | — | 0.2 | — | — | — | — |
| Perfume C | — | — | 0.05 | — | — | — |
| Perfume E | — | — | — | 0.1 | — | — |
| Perfume F | — | — | — | — | 0.05 | — |
| Perfume G | — | — | — | — | — | 0.1 |
| Propylene glycol | 0.06 | — | — | — | 0.1 | — |
| HCl | to pH 4 | to pH 4 | to pH 4 | to pH 4 | to pH 4 | to pH 4 |
| Kathon | 3 ppm | 3 ppm | 3 ppm | 3 ppm | 3 ppm | 3 ppm |
| Distilled water | Bal. | Bal. | Bal. | Bal. | Bal. | Bal. |

EXAMPLES IV

| Examples Ingredients | IVa Wt % | IVb Wt % | IVc Wt % | IVd Wt % | IVe Wt % | IVf Wt % |
|---|---|---|---|---|---|---|
| HPBCD | 1.0 | — | 1.0 | — | 1.0 | — |
| RAMEB | — | 1.0 | — | 1.0 | — | 0.8 |
| Chlorhexidine | 0.01 | 0.02 | 0.01 | 0.01 | 0.05 | 0.05 |
| D5 volatile silicone | 0.5 | 0.5 | 0.5 | 0.35 | — | — |
| PDMS 10,000 cst | — | — | — | 0.35 | — | 0.5 |
| Silwet L-7600 | 0.5 | — | — | — | 0.1 | — |
| Silwet L-7602 | — | 0.5 | — | 0.7 | — | 0.5 |
| Silwet L-7622 | — | — | 0.5 | — | — | — |
| Lithium bromide | — | — | — | 3.0 | — | 2.0 |
| Lithium lactate | — | — | — | — | 3.0 | — |
| Propylene glycol | 0.06 | — | — | — | 0.1 | — |
| Perfume A | 0.1 | — | — | — | — | — |
| Perfume B | — | 0.2 | — | — | — | — |
| Perfume C | — | — | 0.05 | — | — | — |
| Perfume E | — | — | — | 0.1 | — | — |
| Perfume F | — | — | — | — | 0.05 | — |
| Perfume G | — | — | — | — | — | 0.1 |
| Kathon | 3 ppm | 3 ppm | 3 ppm | 3 ppm | 3 ppm | 3 ppm |
| Distilled water | Bal. | Bal. | Bal. | Bal. | Bal. | Bal. |

EXAMPLES V

| Examples Ingredients | Va Wt % | Vb Wt % | Vc Wt % | Vd Wt % | Ve Wt % | Vf Wt % |
|---|---|---|---|---|---|---|
| HPBCD | 1.0 | — | 0.6 | — | 1.0 | — |
| RAMEB | — | 1.0 | — | 1.0 | — | 0.6 |
| Luviset CA 66[a] | 0.4 | — | — | — | — | — |
| Luviset CAP[b] | — | 0.5 | — | — | — | — |
| Sokalan EG 310[c] | — | — | 0.4 | — | — | — |
| Ultrahold CA 8[d] | — | — | — | 1.0 | — | — |
| Amerhold DR-25[e] | — | — | — | — | 0.75 | — |
| Poligen A[f] | — | — | — | — | — | 0.25 |
| Silwet L-7600 | 0.25 | — | — | 0.2 | — | — |
| Silwet L-7602 | — | 0.25 | — | 0.2 | 0.4 | — |
| Silwet L-7604 | — | — | 0.2 | — | — | 0.15 |
| Diethylene glycol | 0.1 | — | 0.1 | 0.2 | 0.2 | 0.15 |
| Propylene glycol | 0.06 | — | — | — | 0.1 | — |
| NaOH/HCl | to pH 9 | to pH 9 | to pH 8 | to pH 8 | to pH 7 | to pH 8 |
| Kathon | 3 ppm | 3 ppm | 3 ppm | 3 ppm | 3 ppm | 3 ppm |
| Distilled water | Bal. | Bal. | Bal. | Bal. | Bal. | Bal. |

[a]Vinyl acetate/crotonic acid copolymer.
[b]Vinyl acetate/vinyl propionate/crotonic acid copolymer.
[c]Polyvinylpyrrolidone/acrylic acid copolymer.
[d]Ethyl acrylate/acrylic acid/N-t-butyl acrylamide copolymer.
[e]Ethyl acrylate/metacrylic acid/methyl methacrylate/acrylic acid copolymer.
[f]Polyacrylate dispersion.

EXAMPLES VI

| Examples Ingredients | VIa Wt % | VIb Wt % | VIc Wt % | VId Wt % | VIe Wt % |
|---|---|---|---|---|---|
| HPBCD | 1.0 | — | 0.5 | — | 0.7 |
| RAMEB | — | 0.5 | — | 1.0 | — |
| Cartaretin F-23[g] | 1.0 | — | — | — | — |
| Copolymer 937[h] | — | 0.3 | — | — | — |
| Copolymer 958[i] | — | — | 0.4 | — | — |
| Diaformer Z-SM[j] | — | — | — | 0.5 | — |
| Vinex 2019[k] | — | — | — | — | 0.5 |
| D5 volatile silicone | 0.25 | — | 0.5 | 0.2 | — |
| PDMS 10,000 cst | — | 0.25 | — | 0.2 | — |
| Silwet L-7600 | 0.3 | — | — | — | 0.1 |
| Silwet L-7602 | — | 0.25 | — | 0.4 | — |
| Silwet L-7622 | — | — | 0.5 | — | — |
| Diethylene glycol | — | — | 0.2 | — | — |
| Propylene glycol | 0.06 | — | — | — | 0.1 |
| Perfume A | 0.1 | — | — | — | — |
| Perfume B | — | 0.05 | — | — | — |
| Perfume C | — | — | 0.05 | — | — |
| Perfume E | — | — | — | 0.1 | — |
| Perfume F | — | — | — | — | 0.05 |
| Perfume G | — | — | — | — | — |
| Kathon | 3 ppm | 3 ppm | 3 ppm | 3 ppm | 3 ppm |

-continued

| Examples Ingredients | VIa Wt % | VIb Wt % | VIc Wt % | VId Wt % | VIe Wt % |
|---|---|---|---|---|---|
| Distilled water | Bal. | Bal. | Bal. | Bal. | Bal. |

(g)Adipic acid/dimethylaminohydroxypropyl diethylenetriamine copolymer.
(h)Polyvinylpyrrolidone/dimethylaminoethyl methacrylate copolymer.
(i)Polyvinylpyrrolidone/dimethylaminoethyl methacrylate copolymer.
(j)Methacryloyl ethyl betaine/methacrylates copolymer.
(k)Polyvinyl alcohol copolymer resin.

EXAMPLES VII

| Examples Ingredients | VIIa Wt % | VIIb Wt % | VIIc Wt % | VIId Wt % | VIIe Wt % | VIIf Wt % |
|---|---|---|---|---|---|---|
| HPBCD | 1.0 | — | 0.6 | — | 1.0 | — |
| RAMEB | — | 0.8 | — | 1.0 | — | 0.5 |
| Copolymer A$^{(l)}$ | 0.4 | 1.0 | — | — | — | — |
| Copolymer B$^{(m)}$ | — | — | 0.3 | 0.6 | — | — |
| PVA$^{(n)}$ | — | — | — | — | 1.0 | 0.5 |
| Velustrol P-40$^{(o)}$ | — | — | — | — | 0.3 | 0.2 |
| D5 volatile silicone | 0.5 | — | — | — | — | — |
| PDMS 1,000 cst | — | — | 0.3 | — | — | 0.2 |
| Silwet L-7600 | 0.5 | — | — | — | 0.25 | 0.25 |
| Silwet L-7602 | — | — | 0.3 | — | — | — |
| Diethylene glycol | — | 1.0 | 0.3 | — | — | 0.3 |
| Propylene glycol | 0.06 | — | — | — | 0.1 | 0.1 |
| Glycerin | — | — | — | — | 0.2 | — |
| Perfume A | 0.1 | — | — | — | — | — |
| Perfume B | — | 0.1 | — | — | — | — |
| Perfume C | — | — | 0.05 | — | — | — |
| Perfume E | — | — | — | 0.1 | — | — |
| Perfume F | — | — | — | — | 0.05 | — |
| Perfume G | — | — | — | — | — | 0.05 |
| NaOH/HCl | to pH 9 | to pH 7 | to pH 9 | to pH 7 | — | — |
| Kathon | 3 ppm | 3 ppm | 3 ppm | 3 ppm | 3 ppm | 3 ppm |
| Distilled water | Bal. | Bal. | Bal. | Bal. | Bal. | Bal. |

(l)Acrylic acid/tert-butyl acrylate copolymer, with an approximate acrylic acid/tert-butyl acrylate weight ratio of about 25/75 and an average molecular weight of from about 70,000 to about 100,000.
(m)Acrylic acid/tert-butyl acrylate copolymer, with an approximate acrylic acid/tert-butyl acrylate weight ratio of about 35/65 and an average molecular weight of from about 60,000 to about 90,000.
(n)Polyvinyl alcohol, about 25,000 average molecular weight.
(o)Oxidized polyethylene emulsion.

The compositions of the above Examples are sprayed onto clothing using, e.g., the TS-800 sprayer from Calmar, and allowed to evaporate off of the clothing.

The compositions of the above Examples are sprayed onto clothing, a kitchen countertop, using a blue inserted Guala® trigger sprayer, available from Berry Plastics Corp. and a cylindrical Euromist II® pump sprayer available from Seaquest Dispensing, respectively, and allowed to evaporate off of the clothing.

The compositions of the above Examples contained in rechargeable battery-operated Solo Spraystar sprayers are sprayed onto large surfaces of fabric, such as several pieces of clothings, and allowed to evaporate off of these surfaces. The level of coverage is uniform and the ease and convenience of application is superior to conventional manually operated trigger sprayers. Consumers prefer this method of application.

The polyalkylene oxide polysiloxane surfactants like the Silwet surfactants provide substantial improvements in the kill of the indicated common organisms when there are antibacterial compounds present. The Pluronic surfactants provide some improvement, but much less.

What is claimed is:

1. A stable, aqueous odor-absorbing composition comprising:

(A) an effective amount to absorb malodors of solubilized, uncomplexed cyclodextrin;

(B) an effective amount to lower the surface tension of the composition, of cyclodextrin compatible surfactant;

(C) an effective amount, to kill, or reduce the growth of microorganisms on a treated surface, of cyclodextrin compatible and water soluble antimicrobial active;

(D) optionally, an effective amount to improve the odor of the composition of hydrophilic perfume containing at least about 50% by weight of the perfume of ingredients having a ClogP of less than about 3.5 and, optionally, a minor amount of perfume ingredients selected from the group consisting of ambrox, bacdanol, benzyl salicylate, butyl anthranilate, cetalox, damascenone, alpha-damascone, gamma-dodecalactone, ebanol, herbavert, cis-3-hexenyl salicylate, alpha-ionone, beta-ionone, alpha-isomethylionone, lilial, methyl nonyl ketone, gamma-undecalactone, undecylenic aldehyde, and mixtures thereof;

(E) optionally, from about 0.01% to about 3% by weight of the composition of low molecular weight polyol;

(F) optionally, from about 0.001% to about 0.3% by weight of the composition of aminocarboxylate chelator;

(G) optionally, an effective amount of metallic salt for improved odor benefit;

(H) optionally, an effective amount of enzyme for improved odor control benefit;

(I) optionally, an effective amount to prevent spoilage of the composition of solubilized, water-soluble, antimicrobial preservative;

(J) an effective amount to remove or noticeably reduce the appearance of wrinkles on fabric of cyclodextrin compatible fabric wrinkle control agent; and (K) aqueous carrier;

wherein the combination of (B) and (C) provides improved antimicrobial activity.

2. The composition of claim 1 wherein said cyclodextrin compatible fabric wrinkle control agent is selected from the group consisting of: cyclodextrin compatible fiber lubricants; cyclodextrin compatible shape retention polymers; cyclodextrin compatible plasticizers; cyclodextrin compatible lithium salts; and mixtures thereof.

3. The composition of claim 2 wherein said cyclodextrin compatible fabric wrinkle control agent is cyclodextrin compatible fiber lubricant.

4. The composition of claim 3 wherein said cyclodextrin compatible fiber lubricant is a silicone.

5. The composition of claim 4 wherein said silicone is volatile and is present at a level of from about 0.1% to about 5%.

6. The composition of claim 5 wherein said volatile silicone has the formula $$[(CH_3)_2SiO]_5.$$

7. The composition of claim 4 wherein said silicone is present at a level of from about 0.1% to about 5% by weight and is selected from the group consisting of:

a. polyalkyl silicone with the following structure:

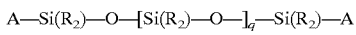

wherein each R is an alkyl, a hydroxy, or a hydroxyalkyl group, and mixtures thereof, having less than about 8 carbon atoms; q is an integer from about 7 to about 8,000; each A is a group selected from hydrogen, methyl, methoxy, ethoxy, hydroxy, and propoxy;

b. silicone having the formula:

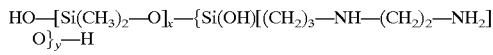

wherein x and y are integers;

c. silicone material having the formula:

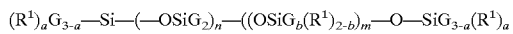

wherein G is selected from the group consisting of hydrogen, OH, and/or $C_1$–$C_5$ alkyl; a denotes 0 or an integer from 1 to 3; b denotes 0 or 1; the sum of n+m is a number from 1 to about 2,000; $R^1$ is a monovalent radical of formula $C_pH_{2p}L$ in which p is an integer from 2 to 4 and L is selected from the group consisting of:

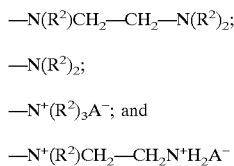

wherein each $R^2$ is chosen from the group consisting of hydrogen, a $C_1$–$C_5$ saturated hydrocarbon radical, and each $A^-$ denotes compatible anion;

d. silicones having the formula:

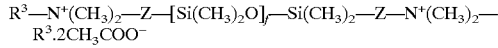

wherein

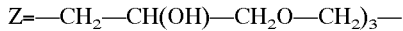

$R^3$ denotes a long chain alkyl group; and f denotes an integer of at least about 2; and e. mixtures thereof.

8. The composition of claim 7 wherein said silicone is polyalkyl silicone

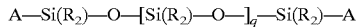

with A and R groups being methyl.

9. The composition of claim 7 wherein said silicone is present at a level of from about 0.2% to about 4% by weight and has a viscosity of from about 10 cst to about 2,000,000 cst.

10. The composition of claim 3 wherein said cyclodextrin compatible fiber lubricant is finely divided polyethylene.

11. The composition of claim 2 wherein said cyclodextrin compatible wrinkle control agent is from about 0.05% to about 10% of shape retention polymer which is a homopolymer and/or a copolymer.

12. The composition of claim 11 wherein the shape retention polymer is homopolymer and/or copolymer having a glass transition temperature of from about –20° C. to about 150° C. and comprising monomers selected from the group consisting of low molecular weight $C_1$–$C_6$ unsaturated organic mono- and polycarboxylic acids; esters of said acids with $C_1$–$C_6$ alcohols; amides and imides of said acids; low molecular weight unsaturated alcohols; esters of said alcohols with low molecular weight carboxylic acids; ethers of said alcohols; polar vinyl heterocyclics; unsaturated amines and amides; vinyl sulfonate; salts of said acids and said amines; $C_1$–$C_4$ alkyl quaternized derivatives of said amines; low molecular weight unsaturated hydrocarbons and derivatives; and mixtures thereof.

13. The composition of claim 11 wherein the shape retention polymer monomers are selected from the group consisting of: acrylic acid, methacrylic acid, crotonic acid, maleic acid and its half esters, itaconic acid; esters of said acids with methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-1-butanol, and mixtures thereof; methyl acrylate; ethyl acrylate; t-butyl acrylate; methyl methacrylate; hydroxyethyl methacrylate; methoxy ethyl methacrylate; N,N-dimethylacrylamide; N-t-butyl acrylamide; maleimides; vinyl alcohol; allyl alcohol; vinyl acetate; vinyl propionate; methyl vinyl ether; vinyl pyrrolidone; vinyl caprolactam; vinyl pyridine; vinyl imidazole; vinyl amine; diethylene triamine; dimethylaminoethyl methacrylate; ethenyl formamide; vinyl sulfonate; ethylene; propylene; butadiene; cyclohexadiene; vinyl chloride; vinylidene chloride; salts thereof and alkyl quaternized derivatives thereof; and mixtures thereof.

14. The composition of claim 11 wherein the shape retention polymer monomers are selected from the group consisting of: vinyl alcohol; acrylic acid; methacrylic acid; methyl acrylate; ethyl acrylate; methyl methacrylate; t-butyl acrylate; t-butyl methacrylate; n-butyl acrylate; n-butyl methacrylate; dimethylaminoethyl methacrylate; N,N-dimethyl acrylamide; N,N-dimethyl methacrylamide; N-t-butyl acrylamide; vinylpyrrolidone; vinyl pyridine; adipic acid; diethylenetriamine; salts thereof and alkyl quaternized derivatives thereof; and mixtures thereof.

15. The composition of claim 11 wherein said cyclodextrin compatible wrinkle control agent is copolymer of hydrophilic monomers and hydrophobic monomers.

16. The composition of claim 15 wherein the shape retention copolymer has a hydrophobic monomer/hydrophilic monomer ratio of from about 95:5 to about 20:80, by weight of the copolymer.

17. The composition of claim 16 wherein the shape retention copolymer has a monomer/hydrophilic monomer ratio of from about 90:10 to about 40:60, by weight of the copolymer.

18. The composition of claim 11 wherein said shape retention polymer is present at from about 0.1% to about 5% by weight, and has a glass transition temperature of from about –10° C. to about 100° C.

19. The composition of claim 2 wherein said cyclodextrin wrinkle control agent is shape retention polymer comprising starch, starch derivatives, and/or mixtures thereof.

20. The composition of claim 2 wherein said cyclodextrin compatible wrinkle control agent is from about 0.01% to about 5% of a hydrophilic plasticizer consisting of short chain polyhydric alcohol.

21. The composition of claim 20 wherein said short chain polyhydric alcohol is selected from the group consisting of: glycerol, ethylene glycol, propylene glycol, diethylene glycol, dipropylene glycol, and mixtures thereof.

22. The composition of claim 2 wherein said cyclodextrin compatible wrinkle control agent is from about 0.1% to about 10% of lithium salt and/or lithium salt hydrate selected from the group consisting of: lithium bromide, lithium lactate, lithium chloride, lithium acetate, lithium sulfate, lithium tartrate, lithium bitartrate, and their hydrates, and mixtures thereof.

23. The composition of claim 22 wherein said lithium salt and/or lithium salt hydrate is selected from the group consisting of: lithium bromide; lithium lactate; their hydrates; and mixtures thereof.

24. The composition of claim 2 wherein said cyclodextrin compatible wrinkle control agent comprises a mixture of fiber lubricant and shape retention polymer.

25. The composition of claim 2 wherein said cyclodextrin compatible wrinkle control agent comprises a mixture of fiber lubricant and lithium salt.

26. The composition of claim 2 wherein said cyclodextrin compatible wrinkle control agent comprises a mixture of shape retention polymer and lithium salt.

27. The composition of claim 2 wherein said cyclodextrin compatible wrinkle control agent comprises a mixture of fiber lubricant, shape retention polymer, and lithium salt.

28. The composition of claim 1 wherein said cyclodextrin is present at a level of from about 0.01% to about 20% by weight of the composition, said surfactant is present at a level of from about 0.01% to about 8% by weight of the composition, said antimicrobial active is present at a level of from about 0.001% to about 0.8% by weight of the composition, and said cyclodextrin is selected from the group consisting of: methyl substituted cyclodextrins, ethyl substituted cyclodextrins, hydroxyalkyl substituted cyclodextrins, branched cyclodextrins, cationic cyclodextrins, quaternary ammonium cyclodextrins, anionic cyclodextrins, amphoteric cyclodextrins, cyclodextrins wherein at least one glucopyranose unit has a 3-6-anhydro-cyclomalto structure, alpha-cyclodextrin, gamma-cyclodextrin, and mixtures thereof.

29. The composition of claim 28 wherein said cyclodextrin is hydroxypropyl beta-cyclodextrin, methylated beta-cyclodextrin, alpha-cyclodextrin, hydroxypropyl alpha-cyclodextrin, methylated alpha-cyclodextrin, and/or mixtures thereof.

30. The composition of claim 28 wherein said cyclodextrin is present at a level of from about 0.01% to about 5% by weight of the composition, said surfactant is present at a level of from about 0.03% to about 5% by weight of the composition, and said antimicrobial active is present at a level of from about 0.002% to about 0.3% by weight of the composition.

31. The composition of claim 30 wherein said cyclodextrin is present at a level of from about 0.5% to about 2%, by weight of the composition, said surfactant is present at a level of from about 0.05% to about 2% by weight of the composition, and said antimicrobial active is present at a level of from about 0.003% to about 0.2% by weight of the composition.

32. The composition of claim 1 wherein said surfactant is selected from the group consisting of: block copolymers of ethylene oxide and propylene oxide; polyalkyleneoxide polysiloxanes; alkyldiphenyl oxide disulfonate anionic surfactants, having the general formula:

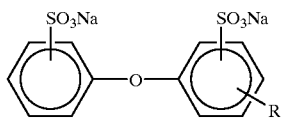

wherein R is an alkyl group; and mixtures thereof.

33. The composition of claim 32 wherein said surfactant is a block copolymer of ethylene oxide and propylene oxide.

34. The composition of claim 32 wherein said surfactant is polyalkyleneoxide polysiloxane having the general formula:

$$R^1-(CH_3)_2SiO-[(CH_3)_2SiO]_a-[(CH_3)(R^1)SiO]_b-Si(CH_3)_2-R^1$$

wherein a+b are from about 1 to about 50, and each $R^1$ is the same or different and is selected from the group consisting of methyl and a poly(ethyleneoxide/propyleneoxide) copolymer group having the general formula:

$$-(CH_2)_nO(C_2H_4O)_c(C_3H_6O)_dR^2$$

with at least one $R^1$ being a poly(ethyleneoxide/propyleneoxide) copolymer group, and wherein n is 3 or 4; total c (for all polyalkyleneoxy side groups) has a value of from 1 to about 100; d is from 0 to about 14; c+d has a value of from about 5 to about 150; and each $R^2$ is the same or different and is selected from the group consisting of hydrogen, an alkyl having 1 to 4 carbon atoms, and an acetyl group.

35. The composition of claim 32 wherein said surfactant is anionic surfactant having the general formula:

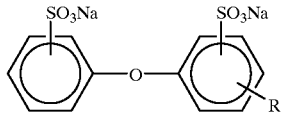

wherein R is an alkyl group.

36. The composition of claim 32 wherein said surfactant provides a surface tension of from about 20 dyne/cm to about 45 dyne/cm.

37. The composition of claim 1 wherein said antimicrobial active is bis-biguanide alkane water soluble salt selected from the group consisting of: chlorides, bromides, sulfates, alkyl sulfonates, phenylsulfonates p-methylphenyl sulfonates, nitrates, acetates, gluconates, and mixtures thereof at a level of from about 0.001% to about 0.4% by weight of the composition.

38. The composition of claim 37 wherein said cyclodextrin is present at a level of from about 0.01% to about 5% by weight of the composition and said bis-biguanide alkane water soluble salt is at a level of from about 0.05% to about 0.2% by weight of the composition and said bis-biguanide alkane water soluble salt is selected from the group consisting of: chlorhexidine; (1) 1,6-bis-(2-ethylhexylbiguanidohexane)dihydrochloride; 1,6-di-($N_1$,$N_1$'-phenyldiguanido-$N_5$,$N_5$')-hexane tetrahydrochloride; 1,6-di-($N_1$,$N_1$'-phenyl-$N_1$,$N_1$'-methyldiguanido-$N_5$,$N_5$')-hexane dihydrochloride; 1,6-di($N_1$,$N_1$'-o-chlorophenyldiguanido-$N_5$,$N_5$')-hexane dihydrochloride; 1,6-di($N_1$,$N_1$'-2,6-dichlorophenyldiguanido-$N_5$,$N_5$')hexane dihydrochloride; 1,6-di[$N_1$,$N_1$'-.beta.-(p-methoxyphenyl) diguanido-$N_5$,$N_5$']-hexane dihydrochloride; 1,6-di($N_1$,$N_1$'-.alpha.-methyl-.beta.-phenyldiguanido-$N_5$,$N_5$')-hexane dihydrochloride; 1,6-di($N_1$,$N_1$'-p-nitrophenyldiguanido-$N_5$, N$_5$')hexane dihydrochloride;.omega.:.omega.'-di-(N$_1$,N$_1$'-phenyldiguanido-N$_5$,N$_5$')-di-n-propylether dihydrochloride;.omega:omega'-di(N$_1$,N$_1$'-p-chlorophenyldiguanido-N$_5$,N$_5$')-di-n-propylether tetrahydrochloride; 1,6-di(N$_1$,N$_1$'-2,4-dichlorophenyldiguanido-N$_5$,N$_5$')hexane tetrahydrochloride; 1,6-di(N$_1$,N$_1$'-p-methylphenyldiguanido-N$_5$,N$_5$')hexane dihydrochloride; 1,6-di(N$_1$,N$_1$'-2,4,5-trichlorophenyldiguanido-N$_5$,N$_5$') hexane tetrahydrochloride; 1,6-di[N$_1$,N$_1$'-.alpha.-(p-chlorophenyl) ethyldiguanido-N$_5$,N$_5$'] hexane dihydrochloride;.omega.:.omega.'di(N$_1$,N$_1$'-p-chlorophenyldiguanido-N$_5$,N$_5$')m-xylene dihydrochloride; 1,12-di(N$_1$,N$_1$'-p-chlorophenyldiguanido-N$_5$,N$_5$')dodecane dihydrochloride; 1,10-di(N$_1$,N$_1$'-phenyldiguanido-N$_5$,N$_5$')-decane tetrahydrochloride; 1,12-di(N$_1$,N$_1$'-phenyldiguanido-N$_5$,N$_5$')dodecane tetrahydrochloride; 1,6-di(N$_1$,N$_1$'-chlorophenyldiguanido-N$_5$,N$_5$')hexane dihydrochloride; 1,6-di(N$_1$,N$_1$'-chlorophenyldiguanido-N$_5$,N$_5$')-hexane tetrahydrochloride; ethylene bis (1-tolyl biguanide); ethylene bis(p-tolyl biguanide); ethylene bis(3,5-dimethylphenyl biguanide); ethylene bis(p-tert-amylphenyl biguanide); ethylene bis(nonylphenyl biguanide); ethylene bis(phenyl biguanide); ethylene bis (N-butylphenyl biguanide); ethylene bis(2,5-diethoxyphenyl biguanide); ethylene bis(2,4-dimethylphenyl biguanide); ethylene bis(o-diphenylbiguanide); ethylene bis(mixed amyl naphthyl biguanide); N-butyl ethylene bis(phenylbiguanide); trimethylene bis(o-tolyl biguanide); N-butyl trimethylene bis (phenyl biguanide); and the corresponding salts of all of the above selected from the group consisting of: the acetates; gluconates; hydrochlorides; hydrobromides; citrates; bisulfites; fluorides; polymaleates; N-coconutalkylsarcosinates; phosphites; hypophosphites; perfluorooctanoates; silicates; sorbates; salicylates; maleates; tartrates; fumarates; ethylenediaminetetraacetates; iminodiacetates; cinnamates; thiocyanates; arginates; pyromellitates; tetracarboxybutyrates; benzoates; glutarates; monofluorophosphates; and perfluoropropionates, and mixtures thereof.

39. The composition of claim 38 wherein said antimicrobial active is chlorhexidine.

40. The composition of claim 1 wherein said water soluble antimicrobial active is quaternary ammonium compound at a level of from about 0.001% to about 0.8% by weight of the composition and is selected from the group consisting of: (1) benzalkonium chlorides; (2) substituted benzalkonium chlorides; (3) di($C_6$–$C_{14}$)alkyl ammonium salt; (4) N-(3-chloroallyl) hexaminium chloride; (5) benzethonium chloride; (6) methylbenzethonium chloride; (7) cetylpyridinium chloride; and (8) mixtures thereof.

41. The composition of claim 1 further comprising at least one additional component selected from the group consisting of (D), (E), (F), (G), (H), (I), and mixtures thereof.

42. An article of manufacture comprising the composition of claim 1 in a spray dispenser.

43. The article of manufacture of claim 42 wherein said spray dispenser comprises a trigger spray device and provides droplets with a weight average diameter of from about 10 to about 120 μm.

44. A method of controlling odor and wrinkles on fabric comprising spraying droplets of an effective amount to control odor and control wrinkles of the composition of claim 1 onto said fabric using a trigger-spray device.

45. The method of claim 44 wherein the droplets of the spray that are formed by the trigger spray device have a weight average diameter of from about 10 to about 120 μm.

46. A method of controlling odor and reducing wrinkles on fabric comprising spraying droplets of an effective amount to control odor and control wrinkles of the composition of claim 1 onto said fabric using a non-manually operated sprayer.

47. The method of claim 46 wherein said non-manually operated sprayer is selected from the group consisting of: powered sprayers; air aspirated sprayers; liquid aspirated sprayers; electrostatic sprayers; and nebulizer sprayers.

48. The method of claim 46 wherein the droplets of the spray that are formed by the non-manually operated sprayer have a weight average diameter of from about 10 to about 120 μm.

49. A stable, aqueous odor-absorbing composition comprising:

(A) an effective amount to absorb malodors of solubilized, uncomplexed cyclodextrin;

(B) an effective amount to lower the surface tension of the composition, of cyclodextrin compatible surfactant;

(C) an effective amount, to kill, or reduce the growth of microorganisms on a treated surface, of cyclodextrin compatible and water soluble antimicrobial active;

(D) optionally, an effective amount to improve the odor of the composition of hydrophilic perfume containing at least about 50% by weight of the perfume of ingredients having a ClogP of less than about 3.5 and, optionally, a minor amount of perfume ingredients selected from the group consisting of ambrox, bacdanol, benzyl salicylate, butyl anthranilate, cetalox, damascenone, alpha-damascone, gamma-dodecalactone, ebanol, herbavert, cis-3-hexenyl salicylate, alpha-ionone, beta-ionone, alpha-isomethylionone, lilial, methyl nonyl ketone, gamma-undecalactone, undecylenic aldehyde, and mixtures thereof;

(E) optionally, from about 0.01% to about 3% by weight of the composition of low molecular weight polyol selected from the group consisting of ethylene glycol, diethylene glycol, propylene glycol, dipropylene glycol, glycerin, and mixtures thereof;

(F) optionally, from about 0.001% to about 0.3% by weight of the composition of aminocarboxylate chelator;

(G) optionally, an effective amount of metallic salt for improved odor benefit;

(H) optionally, an effective amount of enzyme for improved odor control benefit;

(I) optionally, an effective amount to prevent spoilage of the composition of solubilized, water-soluble, antimicrobial preservative;

(J) an effective amount to remove or noticeably reduce the appearance of wrinkles on fabric of cyclodextrin compatible fabric wrinkle control agent; and (K) aqueous carrier;

wherein the combination of (B) and (C) provides improved antimicrobial activity.

* * * * *